US010643747B2

(12) United States Patent
Rudorfer et al.

(10) Patent No.: US 10,643,747 B2
(45) Date of Patent: May 5, 2020

(54) INTELLIGENT SERVICE ASSISTANT INFERENCE ENGINE

(71) Applicant: Siemens Healthcare Diagnostics Inc., Tarrytown, NY (US)

(72) Inventors: Arnold Rudorfer, Princeton, NJ (US); Steve Magowan, Elkton, MD (US); Markus Schmitt, Stamford, CT (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 279 days.

(21) Appl. No.: 15/300,999

(22) PCT Filed: May 19, 2015

(86) PCT No.: PCT/US2015/031529
§ 371 (c)(1),
(2) Date: Sep. 30, 2016

(87) PCT Pub. No.: WO2015/179370
PCT Pub. Date: Nov. 26, 2015

(65) Prior Publication Data
US 2017/0032091 A1    Feb. 2, 2017

Related U.S. Application Data

(60) Provisional application No. 62/000,602, filed on May 20, 2014.

(51) Int. Cl.
G06F 19/00    (2018.01)
G16H 40/40   (2018.01)
(Continued)

(52) U.S. Cl.
CPC ............ G16H 40/40 (2018.01); G06F 19/00 (2013.01); G16H 50/20 (2018.01); G16H 10/40 (2018.01)

(58) Field of Classification Search
CPC .... G06F 19/3412; G06F 19/345; G06F 19/00; G16H 40/40; G16H 50/20; G16H 10/40
See application file for complete search history.

(56) References Cited

U.S. PATENT DOCUMENTS 6,434,572 B2   8/2002 Derzay et al.
6,820,072 B1  11/2004 Skaanning et al.
(Continued)

FOREIGN PATENT DOCUMENTS

WO    2015171581    11/2015

OTHER PUBLICATIONS

International Search Report for PCT/US2015/031529 dated Aug. 19, 2015.

Primary Examiner — Yoshihisa Ishizuka

(57) ABSTRACT

A method of providing dynamic analysis for troubleshooting in vitro diagnostics instrument issues includes receiving, at a second computing device in communication with a plurality of instruments, identification of an issue associated with a portion of an instrument of the plurality of instruments, the identification received from a first computing device in communication with the instrument. A central computing device accesses data from one or more databases and determines an ordering of one or more corrective actions for resolving the issue by applying the data to a probabilistic model based on at least one of: patterns from the plurality of instruments; and operator input. The central computing device provides the one or more corrective actions in the determined order to the first computing device to be displayed via a user interface at the instrument.

16 Claims, 26 Drawing Sheets

(51) Int. Cl.
*G16H 50/20* (2018.01)
*G16H 10/40* (2018.01)

(56) References Cited

U.S. PATENT DOCUMENTS

| | | |
|---|---|---|
| 7,096,067 B2 | 8/2006 | Linberg |
| 7,373,552 B2 | 5/2008 | Bjoersne |
| 8,437,904 B2 | 5/2013 | Mansouri et al. |
| 2007/0198213 A1* | 8/2007 | Parvin .................. G16H 10/40 702/179 |
| 2008/0186134 A1 | 8/2008 | Parkhurst et al. |
| 2011/0070587 A1 | 3/2011 | Fuernkranz et al. |
| 2012/0011253 A1 | 1/2012 | Friedman et al. |
| 2013/0066563 A1 | 3/2013 | Hengstler et al. |
| 2013/0338450 A1 | 12/2013 | Osorio et al. |
| 2014/0095191 A1 | 4/2014 | Kabbani et al. |

\* cited by examiner

| PROBABILITY | DESCRIPTION | RESOLUTION |
|---|---|---|
| 95% | Bio-Rad QC Control Product Lot TX123123 Recalled by Vendor | Replace Product |
| 5% | Quvette Ring Temperature High (37.34Q) | Adjust Ring Temperature |

FIG. 7

- If <no test result after 1 hour> then check reagent status on Clinical Chemistry analyzer
  - If <reagent status = OK> then
  - If <calibration for onboard lot = expired> then
    - If <Quality Control status = failed> then {
      - notify customer service engineer on issue
      - Provide customer service engineer with case # to retrieve on how to fix a failure Quality Control on the Clinical Chemistry analyzer}

FIG. 22

INTELLIGENT SERVICE ASSISTANT INFERENCE ENGINE

CROSS-REFERENCE TO RELATED APPLICATIONS

This application claims priority to U.S. provisional application Ser. No. 62/000,602, filed May 20, 2014, which is incorporated herein by reference in its entirety.

TECHNOLOGY FIELD

The present invention relates generally to servicing in vitro diagnostic instruments, and more particularly to systems and methods for dynamically identifying solutions for troubleshooting issues related to in vitro diagnostic instruments that generate analytical test results from a patient's bodily fluids.

BACKGROUND

In-Vitro Diagnostics (IVD) allows laboratories to assist in the diagnosis of disease based on assays performed on patient fluid samples. IVD includes various types of analytical tests and assays typically conducted with automated clinical chemistry analyzers (analyzers) onto which fluid containers, such as tubes or vials containing patient samples (e.g., blood samples), have been loaded. The analyzer extracts a fluid sample from the vial and combines the sample with various reagent fluids (reagents) in special reaction cuvettes or tubes (referred to generally as reaction vessels).

IVD instruments are typically serviced at regular intervals for proper functioning to deliver tests to labs and doctors. When non-scheduled instrument issues occur, instrument uptime, operator workflow and efficiency are affected.

Conventional methods for troubleshooting IVD instrument issues are complex (e.g., identification of root causes of issues) and time consuming (e.g. time to determine correct path for a solution). These conventional methods rely on operator knowledge to fix the issues, thereby increasing operator workflow. Some conventional methods for troubleshooting IVD instruments issues include identifying the issues through an error condition or error code. In these conventional methods, an operator may look up how to troubleshoot an issue in a printed manual based on the error condition or error code. Operators may also search online for troubleshooting issues. Other conventional methods for troubleshooting IVD instruments issues include identifying the issues through a representative via the telephone phone or online. These conventional methods which include defining an issue and identifying solutions/strategies are time consuming and inefficient.

SUMMARY

Systems, methods, and apparatuses are described herein which relate generally to the dynamic identification of solutions for troubleshooting issues related to in vitro diagnostic instruments that generate analytical test results from a patient's bodily fluids. According to some embodiments, a method of providing dynamic analysis for troubleshooting in vitro diagnostics instrument issues includes receiving, at a second computing device in communication with instruments an identification of an issue associated with a portion of an instrument of the instruments. This issue is provided by a first computing device in communication with the instrument and may be, for example, software-related, hardware-related, or assay-related. A central computing device accesses data from one or more databases. The data may include, for example, calibration data, call center data, data logs from related instruments, vendor data, expert-built rule data, expert-built strategy data, and/or static troubleshooting data. Once the data is accessed, the central computing device determines an ordering of one or more corrective actions for resolving the issue by applying the data to a probabilistic model based at least one of: patterns from the instruments; and operator input. The patterns from the instruments may include, for example, success patterns from the instruments; and/or failure patterns from the instruments. The operator input may include, for example, feedback relating to the instrument; identification of the issue; and/or data indicating a navigation path with steps taken to attempt to resolve the issue.

In some embodiments of the aforementioned method, the central computing device provides the one or more corrective actions in the determined order to the first computing device to be displayed via a user interface at the instrument. The order of the one or more corrective actions may be based, for example, on a probability to resolve the issue. In some embodiments the ordering of the one or more corrective actions for resolving the issue is incorporated into a report.

In some embodiments, the method further includes the central computing device receiving an identification of a successful corrective action from the one or more corrective actions from the associated computing device. Data in the database may then be updated to indicate the successful corrective action. Data in one or more local databases may also be updated, with each local database associated with a respective computing device on an instrument. In some embodiments the updating of data may be performed in real-time or at regular intervals.

According to other embodiments, a system for providing dynamic analysis for troubleshooting in vitro diagnostics instrument issues includes, in vitro diagnostics instruments; one or more computing devices, a central computing device in communication with the one or more computing devices and one or more databases in communication with the central computing device. Each computing device is in communication with an instrument of the in vitro diagnostics instruments and each computing device comprising a user interface having a display. The central computing device is configured to receive identification of an issue associated with a portion of the instrument from the corresponding computing device in communication with the instrument. This issue may be, for example, software-related, hardware-related, or assay-related. The central computing device is further configured to access data from the one or more databases and apply the data to a probabilistic model to determine an ordering of one or more corrective actions for resolving the issue. The ordering of the one or more corrective actions may be based, for example on likeliness to resolve the issue. In some embodiments, the probabilistic model based on at least one of: patterns from related instrument and operator input. For example, the patterns from the related instruments may include success patterns from related instruments and/or failure patterns from related instruments. The input from an operator may include, for example, one or more of (i) feedback relating to the instrument, (ii) identification of the issue, and (iii) data related to a navigation path indicating steps taken to attempt to resolve the issue. Once the ordering of one or more corrective actions for resolving the issue is determined, the central computing device may provide the one or more corrective actions in the determined order to the computing device to be displayed via the user interface at the instrument.

Various enhancements, refinements, or other modifications may be made to the aforementioned system in some embodiments. For example, the data used in the aforementioned method may include one or more of calibration data, call center data, data logs from related instruments, vendor data, expert-built rule data, expert-built strategy data, and static troubleshooting data. In some embodiments, the one or more databases are continuously updated to reflect issues and solutions. In some embodiments, the central computing device is further configured to incorporate the ordering of the one or more corrective actions for resolving the issue into a report.

In some embodiments of the aforementioned system, the central computing device is further configured to: receive, from the corresponding computing device in communication with the instrument, identification of a successful corrective action from the one or more corrective actions; update data in one or more of the one or more databases to indicate the successful corrective action; and update data in one or more local databases, each local database associated with a respective computing device on a respective instrument. The updating step may be performed, for example, in real-time or at regular intervals.

Additional features and advantages of this disclosure will be made apparent from the following detailed description of illustrative embodiments that proceeds with reference to the accompanying drawings.

BRIEF DESCRIPTION OF THE DRAWINGS

The foregoing and other aspects of the embodiments disclosed herein are best understood from the following detailed description when read in connection with the accompanying drawings. For the purpose of illustrating the embodiments disclosed herein, there is shown in the drawings embodiments that are presently preferred, it being understood, however, that the embodiments disclosed herein are not limited to the specific instrumentalities disclosed. Included in the drawings are the following Figures:

FIG. 6 is a screen shot illustrating an exemplary prompt to a user to indicate one or more corrective actions to successfully resolve the identified issue shown in FIG. 4;

FIG. 7 is a screen shot illustrating an exemplary updated list that is ordered based on a probability of the corrective actions to successfully solve the issue shown in FIG. 4;

FIG. 22 illustrates a fourth set of steps in the RBR example that may be implemented using some embodiments;

DESCRIPTION OF EXEMPLARY EMBODIMENTS

Embodiments provide an intelligent service assistant (ISA) inference engine that dynamically identifies issues and solution strategies in real time and enables operators of IVD instruments to resolve system hardware, software, and assay issues.

The ISA Inference Engine is configured to define and develop issues and solution strategies through semi-automated to automated reasoning capabilities, using an expert system approach. The ISA Inference Engine includes an ISA rules base configured to encode customer service knowledge on issues and solution strategies in the form of IF, THEN statements and an ISA Rules Engine that include rules that link the issues and solution strategies to a conclusion.

Embodiments provide benefits such as, for example, scalability, as more rules are defined, formulated, and tested; rule authoring and testing; collaboration in use of rule repository: reuse of existing rules, flows, and models; simulation of rule engine runs: load, assert/retract, and perform inference; rules tracking and version control; monitoring of changes of rules over time; management of multi-user access; and a rules language.

The ISA Rules Engine is a software application designed to produce reasoning on rules formulated by the customer service engineer. The ISA Rules Engine has a batch mode (processing of rules in a set) and a conversational mode (constructing rules step-by-step). The ISA Rules Engine has the following functionality: reasoning capability in a probabilistic (non-deterministic) nature, to relate issues to solution strategies; automated identification of best-fit solution strategies to troubleshoot an issue across a fleet of instruments; evaluation of operator's feedback as a means to grade success of employed solution strategies; on-demand report generation of most effective solution strategies per issue; trend analysis of product components that need re-design based on the characteristics of customer fixes; and re-prioritization of solution strategies based on reported success from operators across a fleet of instruments.

Instrument Side Software Client

Figure 1:
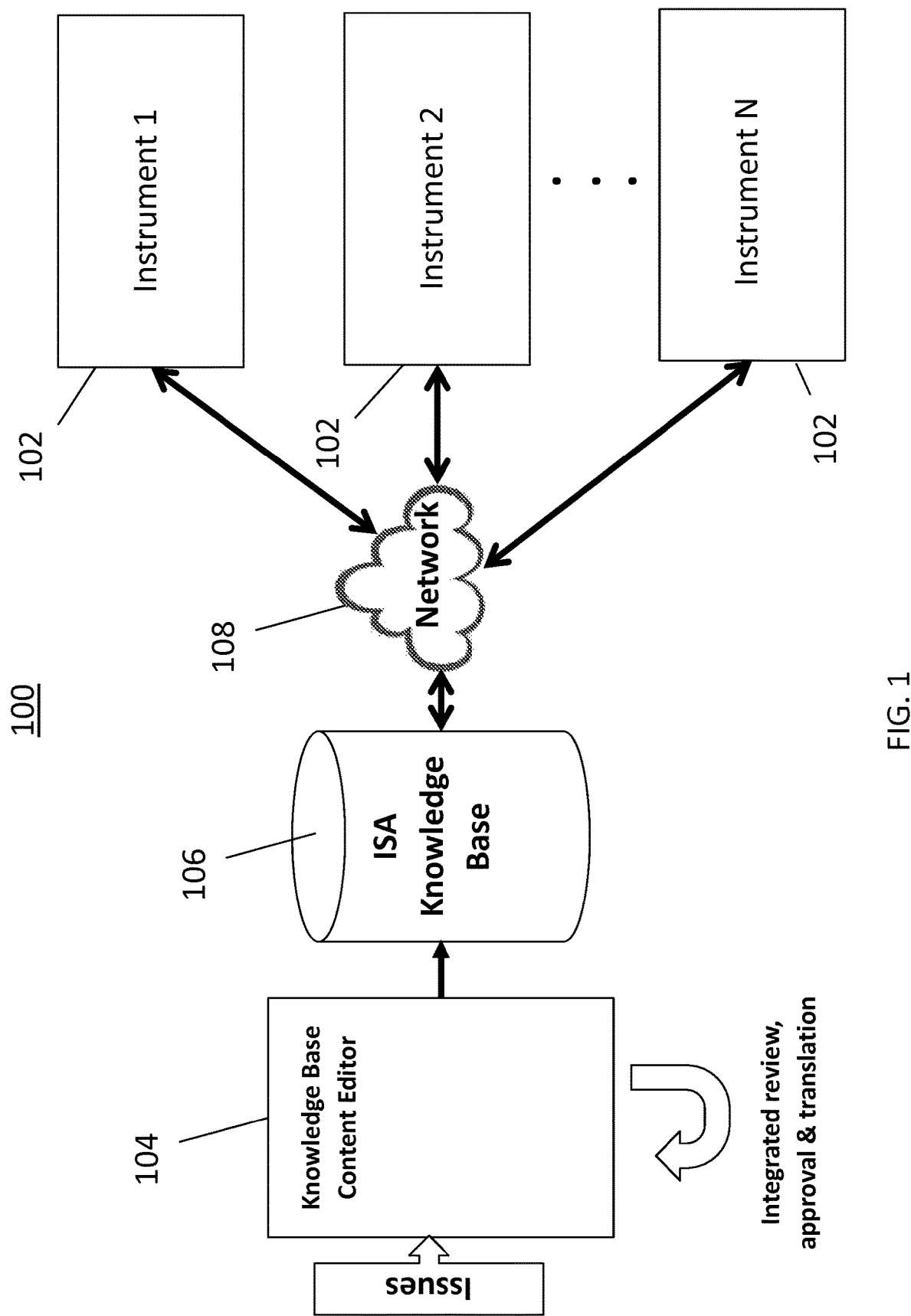
FIG. 1 is a system diagram of an exemplary system of providing troubleshooting for an in vitro diagnostics instrument according to embodiments disclosed herein.
Figure 2:
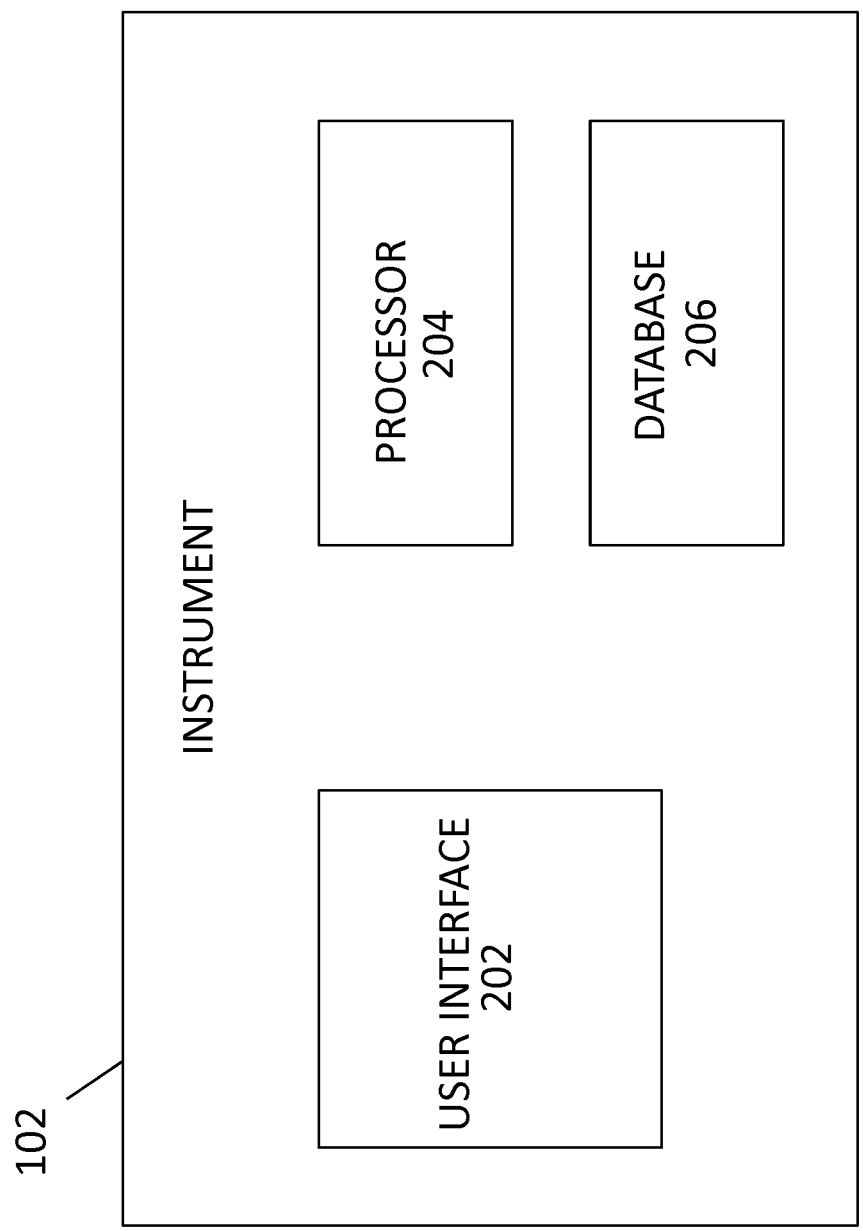
FIG. 2 is a block diagram illustrating an exemplary instrument of the system shown in FIG. 1.

FIG. 1 is a system diagram of an exemplary ISA system 100 of providing troubleshooting for an in vitro diagnostics instrument 102 according to embodiments disclosed herein. FIG. 2 is a block diagram illustrating an exemplary in vitro diagnostics instrument 102 of ISA system 100 shown in FIG. 1. Referring generally to FIG. 1 and FIG. 2, the ISA system 100 includes in vitro diagnostics instruments 102. Embodiments may include ISA systems having any number of instruments. Each instrument may have a database dedicated to itself. For example, as shown in FIG. 2, an in vitro diagnostics instrument 102 may include a dedicated database 206. Database 206 may be configured to store a plurality of issues each associated with a portion of the in vitro diagnostics instrument 102 and a plurality of corrective actions for resolving corresponding issues. The in vitro diagnostics instrument 102 may also include a user interface 202 (e.g., a graphical user interface (GUI)) comprising one or more display elements configured to provide user interaction to identify an issue of the plurality of issues associated with a portion of the in vitro diagnostics instrument 102. The in vitro diagnostics instrument 102 may also include a computing device, such as processor 204 dedicated to an in vitro diagnostics instrument 102, in communication with the user interface 202. The processor 204 may be configured to receive the identification of the issue and to determine one or more of the plurality of corrective actions for resolving the issue. The user interface 202 may be configured to display an ordered list of the one or more corrective actions for resolving the issue and receive an indication of the one or more corrective actions that successfully resolved the issue.

As shown in FIG. 1, the ISA system 100 may also include a second computing device, such as a knowledge base content editor 104, and a second database, ISA Knowledge Base 106 in communication with the knowledge base content editor 104. In some aspects, the knowledge base content editor 104 may be a central computing device in communication with each of the in vitro diagnostics instruments 102. In some aspects, the ISA Knowledge Base 106 may be a central database in communication with each of the in vitro diagnostics instruments 102. For example, as shown in FIG. 1, the knowledge base content editor 104 and the ISA Knowledge Base 106 are in communication with each of the in vitro diagnostics instruments 102 via network 108.

The ISA Knowledge Base 106 may include identified issues with related solution strategies. Various users, such as development engineers and customer service engineers may access the knowledge base content editor 104 to create and/or edit issues that are encountered, carry out a root cause analysis, and derive applicable solution strategies for remedying the issue. Each issue, with its set of solution strategies, may be stored in the ISA Knowledge Base 106.

Embodiments may include any number of computing devices and any number of data bases. For example, in vitro diagnostics instruments 102 may include subsets of instruments with the instruments of each subset being in communication with a corresponding communication device. Each communication device in communication with the instruments of each subset may, in turn, be in communication with a central communication device. Network 108 may be a wide area network or a local area network. Network 108 may also include a plurality of networks.

In some embodiments, a database 206 dedicated to an in vitro diagnostics instrument 102 may be a part (e.g., within the instrument) of an in vitro diagnostics instrument 102. In other embodiments, a database 206 may be dedicated to the in vitro diagnostics instrument 102 while being disposed remote from the in vitro diagnostics instrument 102.

In some embodiments, an in vitro diagnostics instrument 102 may not include a database 206. That is, ISA Knowledge Base 106 may be configured to store the plurality of issues associated with portions of each of the in vitro diagnostics instruments 102 and a plurality of corrective actions for resolving corresponding issues.

In some embodiments, the computing device is in communication with one or more other computing devices configured to receive indications of corresponding corrective actions determined to successfully resolve the issue at other instruments and provide the corresponding corrective actions to the computing device.

Figure 3:
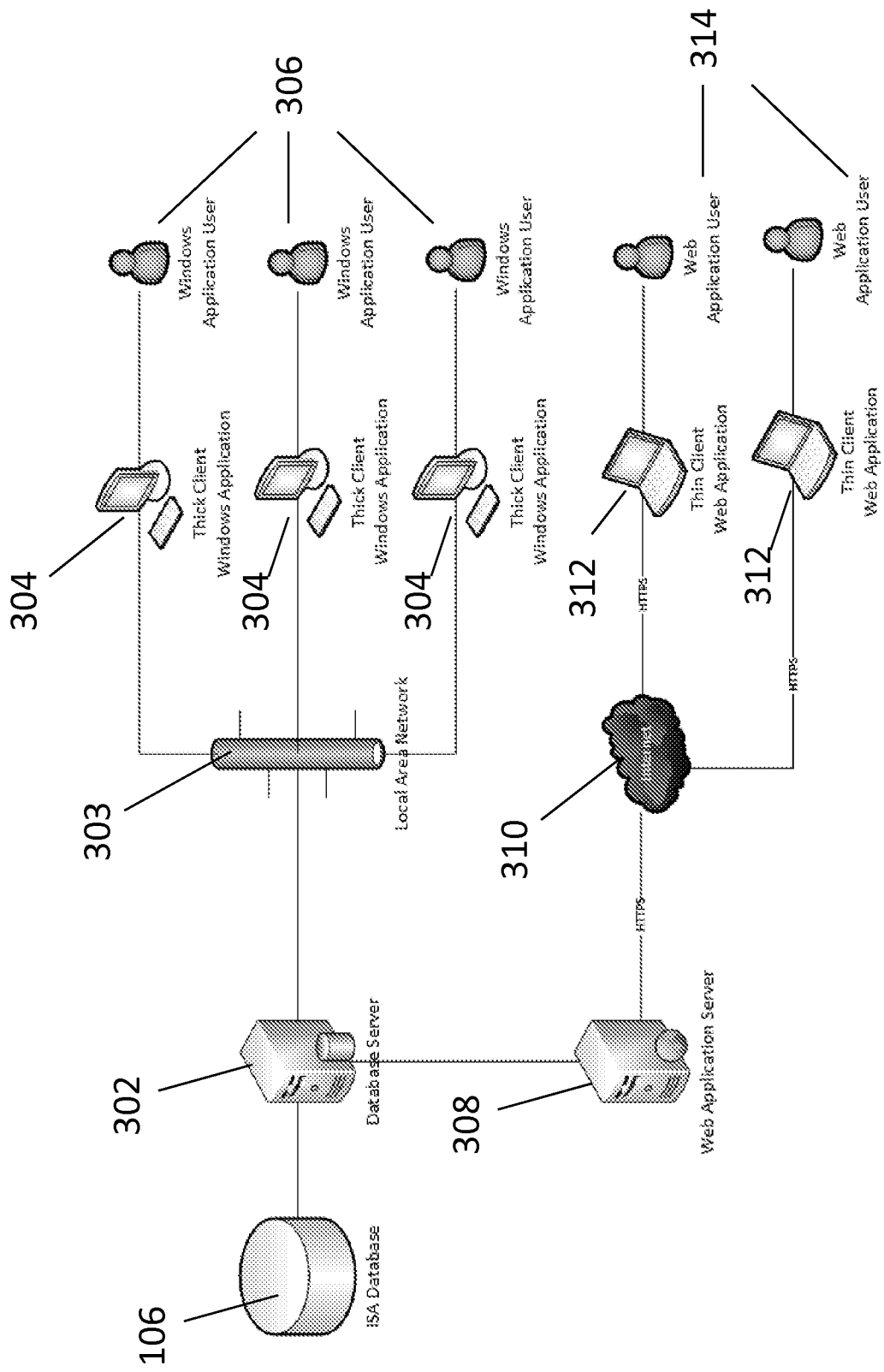
FIG. 3 is an illustration of an exemplary configuration of a communication architecture that may be used with embodiments disclosed herein.

FIG. 3 is an illustration of an exemplary configuration of a communication architecture that may be used with embodiments disclosed herein. For example, as shown in FIG. 3, ISA Knowledge Base 106 may be in communication with a database server 302. The database server 302 may be in communication with any number of clients, such as thick clients 304 (e.g., windows application thick client) via local area network 303. Thick clients 304 may provide users 306 with more features, graphics and choices than thin clients 312 provide users 314, thus providing more customizable applications. Processing for thick clients 304 may be performed locally on the user system (e.g., in vitro diagnostics instrument 102), and may not rely heavily on a central processing server, such as database server 302. The database server 302 may be accessed primarily for storage purposes. For example, the computing devices (e.g., processor 204 in FIG. 2) in communication with in vitro diagnostics instruments 102 may be thick clients. In some embodiments, the computing devices (e.g., processor 204 in FIG. 2) in communication with in vitro diagnostics instruments 102 may be thin clients that rely more heavily on a central processing server.

The database server 302 may also be in communication with a web application server 308. The web application server 308 may be in communication with any number of clients, such as thin clients 312 (e.g., web application thin client) via a wide area network, such as the internet 310. In some embodiments, the communication system architecture may include any number of web application servers 308 in communication with clients via any number of wide area networks within the internet 310. Thin clients 312 may include less hardware and software than thick clients 304 and may rely more heavily on a remote server, such as database server 302, allowing thin clients 312 to be centrally managed via software deployed on a central server, such as web application server 308, instead of each thin client 312.

Exemplary methods of providing troubleshooting for an in vitro diagnostics instrument are now described. The method may include receiving, via a computing device, identification of one of a plurality of issues of the instrument, each of the plurality of issues associated with a portion of the instrument. For example, an issue may occur and be identified by processor 204.

In some embodiments, the in vitro diagnostics instrument 102 may be self-aware of error conditions (e.g., a vessel with a sample is stuck on an internal transport system (from and to an analyzer)) and an event code or error code may be automatically generated (e.g., by a processor, such as processor 204, using instrument software) when an issue occurs. In other embodiments, the operator's selection of (e.g., selection of key words) via an interface, such as user interface 202, may provide a structured operator-defined issue for the instrument software to be translated into a non-event code or issue code, which may be rendered as an alpha-numeric code. Alpha-numeric codes may be received (e.g., by knowledge base content editor 104 and/or processor 204) when the ISA software client is launching. The alpha-numeric code may identify the issue and provide (e.g., via a link) an operator with the correct content in the user interface 202. The user interface 202 may prompt the operator to launch the ISA by selecting (e.g., via a button, a portion of a touch screen, or the like) on the user interface 202. In some embodiments, content may be provided to an operator in a wizard style format.

Figure 4:
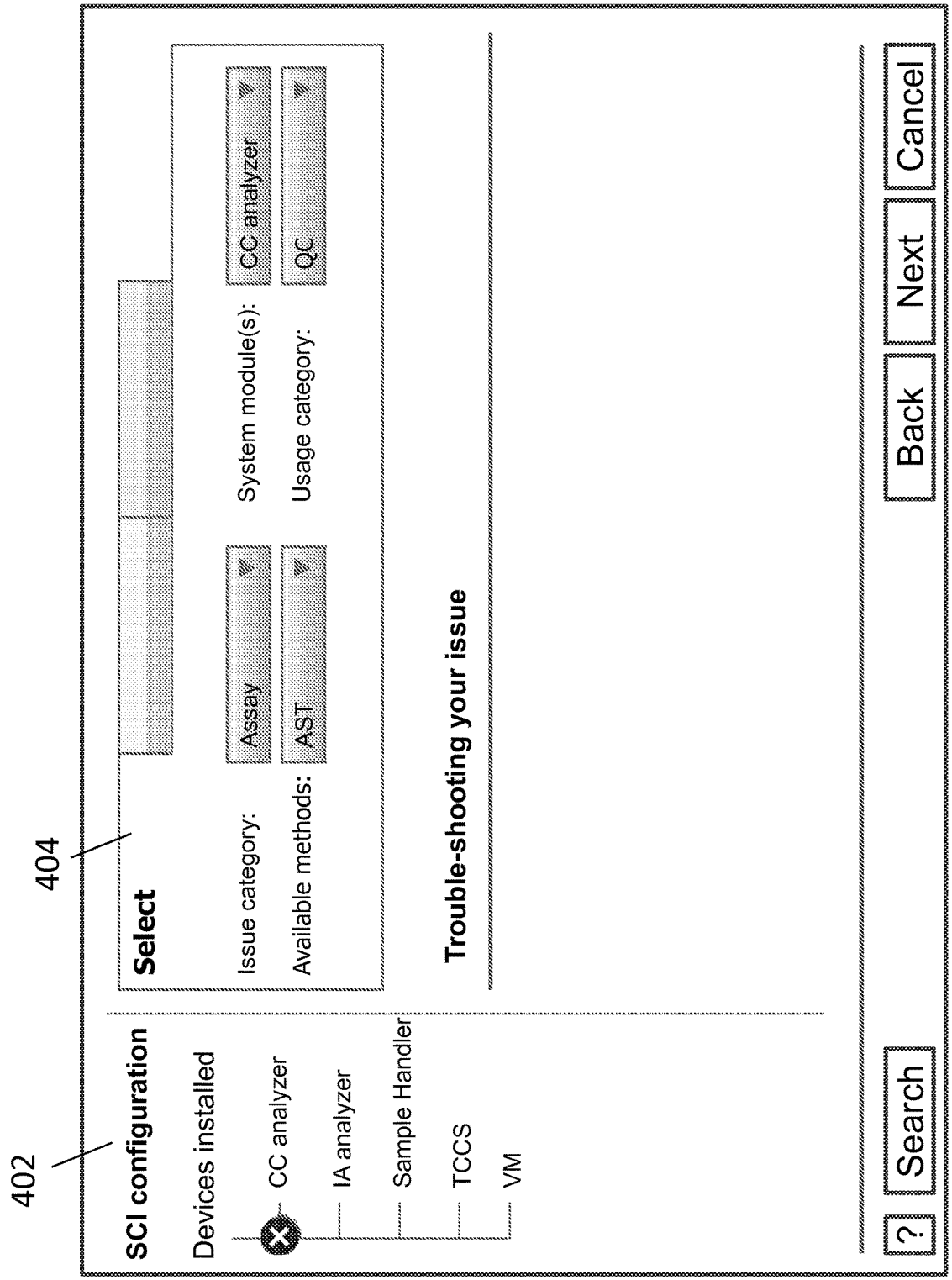
FIG. 4 is a screen shot illustrating an exemplary identification of an instrument issue according to an embodiment.

FIG. 4 is an exemplary screen shot illustrating an exemplary identification of one of a plurality of issues of the in vitro diagnostics instrument 102. As shown in FIG. 4, the instrument configuration of installed devices (e.g., clinical chemical (CC) analyzer, an immunoassay (IA) analyzer and a sample handler) may be displayed in area 402.

Figure 5:
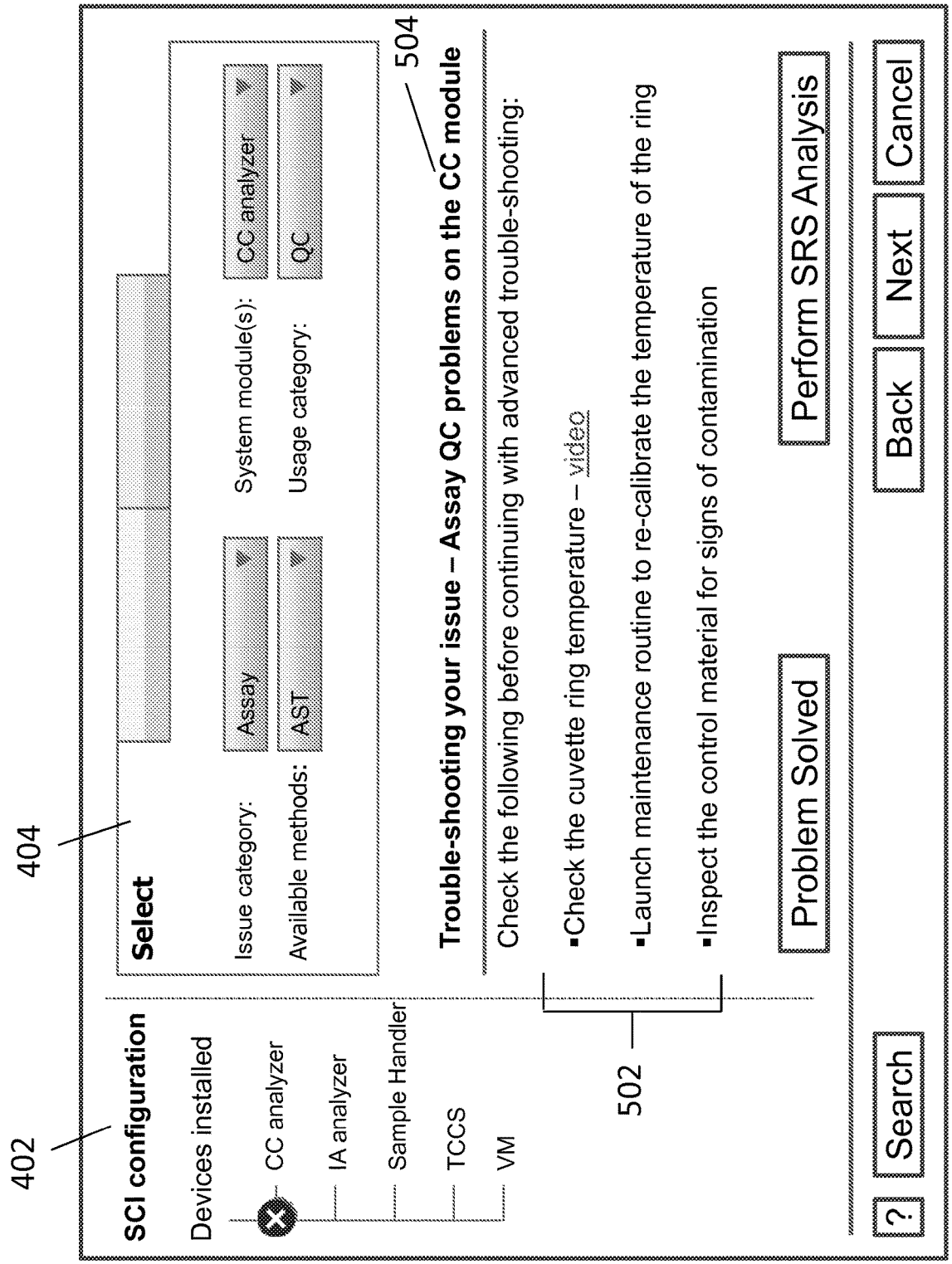
FIG. 5 is a screen shot illustrating an exemplary ordered list of corrective actions displayed to resolve the identified issue shown in FIG. 4.

In the example shown in FIG. 5, the issue 504 is identified as "Assay QC problems on the CC module." A processor, such as processor 204, may automatically determine the issue 504 and generate an event code or error code. As shown in FIG. 5, the CC analyzer may be indicated (e.g., via "X" shown in FIG. 4) as having an event code. Selectable options corresponding to different categories may be automatically determined (e.g., via a processor, such as processor 204) and displayed using the event code, as shown in area 404. For example, the categories shown in FIG. 4 include: Issue category; Available methods; System module; and Usage category. The selectable options for each category are automatically selected as: Issue Category: Assay; System Module: CC Analyzer; Available Methods: AST; and Usage Category: quality control (QC). The categories and selectable options shown in FIG. 4 are exemplary. Embodiments may include categories and selectable options different than those shown in FIG. 4. In some embodiments, the operator may select the options for each category. For example, if no event code is available or only a generic event code is available, the operator may define a scope around the issue by triangulating the problem. When an issue is identified, an ordered list of one or more corrective actions may be provided to resolve the identified issue.

FIG. 5 is an exemplary screen shot illustrating a displayed ordered list 502 of corrective actions to resolve an identified issue 504. The ordered list 502 may be stored in a database, such as database 206. The ordered list 502 may be retrieved from database 206 and displayed via a user interface, such as user interface 202. In the example shown in FIG. 5, the issue is identified as "Assay QC problems on the CC module."

The ISA Knowledge Base 106 may include the encoded customer service knowledge on how to troubleshoot an instrument issue. In one embodiment, the problem statement and its corrective actions may be rendered in a decision-tree style format. For example, as shown in FIG. 5, the ordered list 502 of corrective actions is displayed in the following order: (1) Check the cuvette ring temperature—video; (2) Launch maintenance routine to re-calibrate the temperature of the ring; and (3) Inspect the control material for signs of contamination. The issue 504 displayed in FIG. 5 is merely exemplary. Embodiments may include issues different from the issue displayed in FIG. 5. The ordered list 502 of corrective actions displayed in FIG. 5 is also exemplary. Embodiments may include ordered lists different from the ordered list 502 displayed in FIG. 5 and may include any number of corrective actions. A video or other resource can be provided with each potential corrective action.

In some embodiments, ordered lists of corrective actions for solving issues may be stored in databases (e.g., instrument database 206) prior to operation of instruments (e.g., at the time of instrument manufacturing). In other embodiments, ordered lists of corrective actions for solving issues may be provided to instruments, via one or more networks, after an instrument is in its place of operation.

Referring back to FIG. 5, the operator of the in vitro diagnostics instrument 102 may review the ordered list 502 of corrective actions. The operator may check the temperature of a cuvette ring, launch a maintenance routine to re-calibrate the temperature of the cuvette ring and recalibrate the assay and perform a test using a third party QC material to verify if corrective actions were successful. If the issue is resolved by one or more of the corrective actions, an indication may be received that one or more corrective actions successfully resolved the issue 504.

Figure 6:
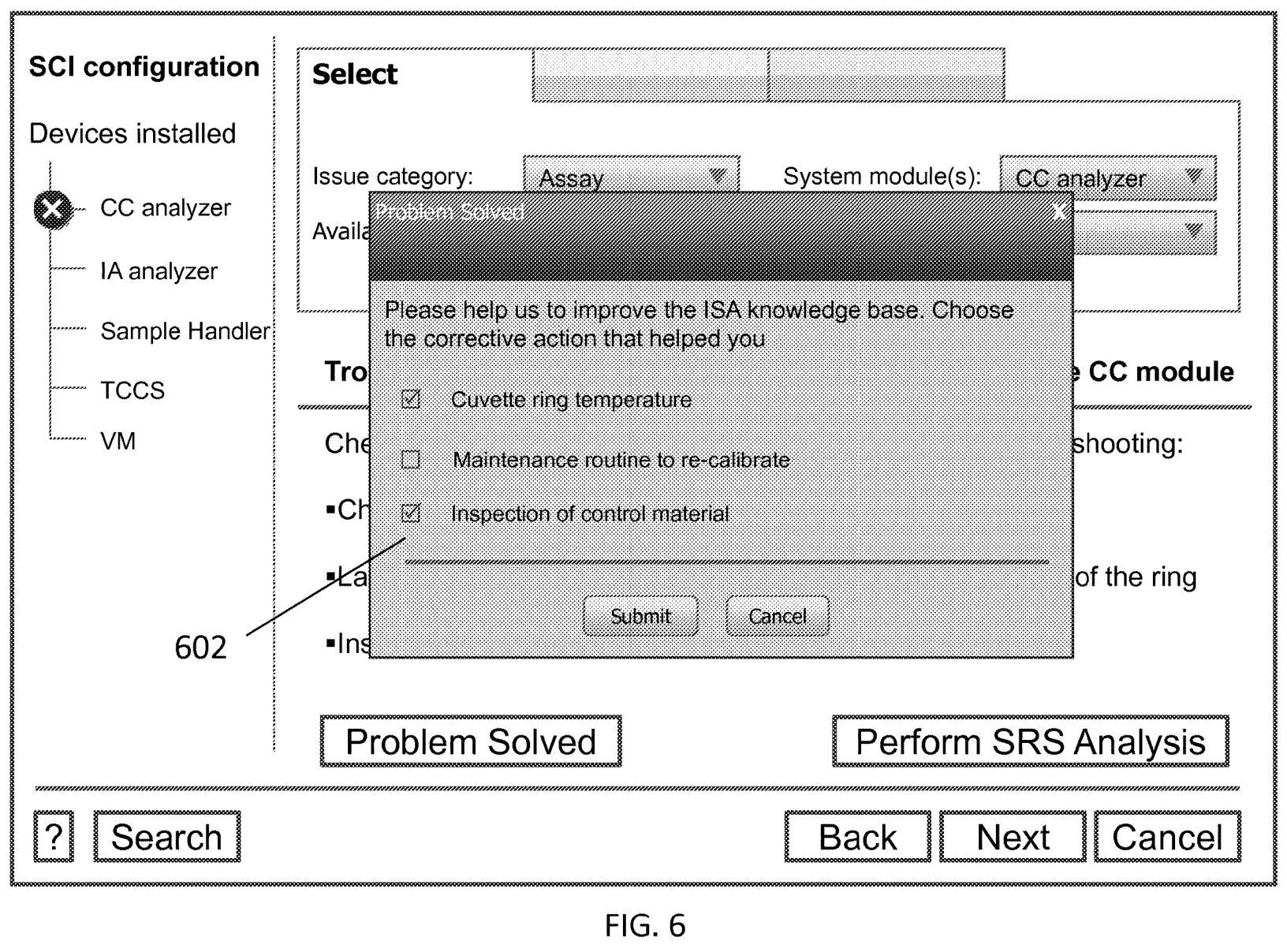

FIG. 6 is a screen shot illustrating an exemplary prompt area 602 prompting a user to indicate one or more of the corrective actions displayed in the ordered list 502 (shown in FIG. 5) to successfully resolve the identified issue 504 (shown in FIG. 5). In some embodiments, the user interface 202 may be used to prompt the operator and to receive the indication of one or more successful corrective actions. The indication may then be received by a computing device, such as processor 204. For example, as shown in FIG. 6, prompt area 602 prompts the user to choose which corrective actions (cuvette ring temperature, maintenance routine to recalibrate and inspection of control material) helped the operator. The corrective actions that were successfully used may be indicated (as shown by checkmarks) by as cuvette ring temperature and inspection of control material. In another embodiment, one or more corrective actions may be automatically determined (e.g., via one or more sensors and one or more processors) to have successfully solved the issue. In some embodiments, the successful corrective actions may be stored locally at the instrument (e.g., database 206) and then sent to a second database, such as ISA Knowledge Base 106 (shown in FIG. 1) in communication with a plurality of in vitro diagnostics instruments 102 via one or more networks, such as network 108 (shown in FIG. 1). In other embodiments, the successful corrective actions may be sent to the second database without being stored at a local database.

In some embodiments, a report may be created that includes (i) the one or more corrective actions determined to successfully resolve the instrument issue and (ii) a navigation path indicating one or more steps used to provide the one or more corrective actions determined to successfully resolve the instrument issue. In some aspects, the report may be created by a local computing device (e.g., database 206) and then sent to a second database, such as ISA Knowledge Base 106. In other embodiments, the report may be sent to the second database without being stored at a local database. The successful corrective actions and/or the reports may be sent to the second database in equal time intervals (e.g., per hour, per day, per week), responsive to an event occurring, or on demand.

The second database (e.g., database in communication with a plurality of in vitro diagnostics instruments 102, such as ISA Knowledge Base 106), may receive the successful corrective actions and/or the reports and may analyze the corrective actions and/or reports. The analysis may include associating the corrective actions with corresponding issues and determining updated ordered lists of the corrective actions for each corresponding issue. The updated lists may then be sent to one or more in vitro diagnostics instruments 102 in equal time intervals (e.g., per hour, per day, per week), responsive to an event occurring, or on demand.

FIG. 7 is a screen shot illustrating an exemplary updated list 702 that is ordered based on a probability of the corrective actions to successfully solve the issue 504. As shown in FIG. 7, the first corrective action (Replace Product) of the updated list 702 includes a 95% probability of successfully solving the issue 504. The second corrective action (Adjust Ring Temperature) of the updated list 702 includes a 5% probability of successfully solving the issue 504. As shown, each corrective action may also include a description section having additional information.

The updated list shown in FIG. 7 is exemplary. Embodiments may include updated lists that are ordered based on: a success rate as indicated at each of the in vitro diagnostics instruments 102; a probability of the corrective actions to successfully solve each corresponding issue; and; a priority. The updated list may include: the same corrective actions as the previous list but in a different order; one or more corrective actions that were not in the previous list; and one or more corrective actions removed from the previous list.

A central computing device, such as ISA Knowledge Base Content Editor 104, may interface with any number of memory devices, such as read only memory (ROM), random access memory (RAM), and one or more optional non-transitory memory devices such as, for example, an external or internal DVD drive, a CD ROM drive, a hard drive, flash memory, a USB drive, or the like. The memory devices may be configured to include individual files and/or one or more databases for storing any software modules, instructions, or data.

Program instructions, software, or interactive modules for performing any of the functional steps associated with the processes as described above may be stored in the ROM and/or the RAM. Optionally, the program instructions may be stored on a tangible computer readable medium such as a compact disk, a digital disk, flash memory, a memory card, a USB drive, an optical disc storage medium, such as a Blu-Ray™ disc, and/or other recording medium.

A display interface, such as a display included in user interface 202, may permit information from the ISA to be displayed on the display in audio, visual, graphic, and/or alphanumeric format. Communication with external devices may occur using various communication ports that may be attached to one or more communications networks, such as the Internet or a local area network, or directly to a portable computing device such as a notebook computer. The user interface 202 may allow for receipt of data from input devices such as a keyboard, a mouse, a joystick, a touch screen, a remote control, a pointing device, a video input device, an audio input device, and the like.

Inference Engine

Figure 8:
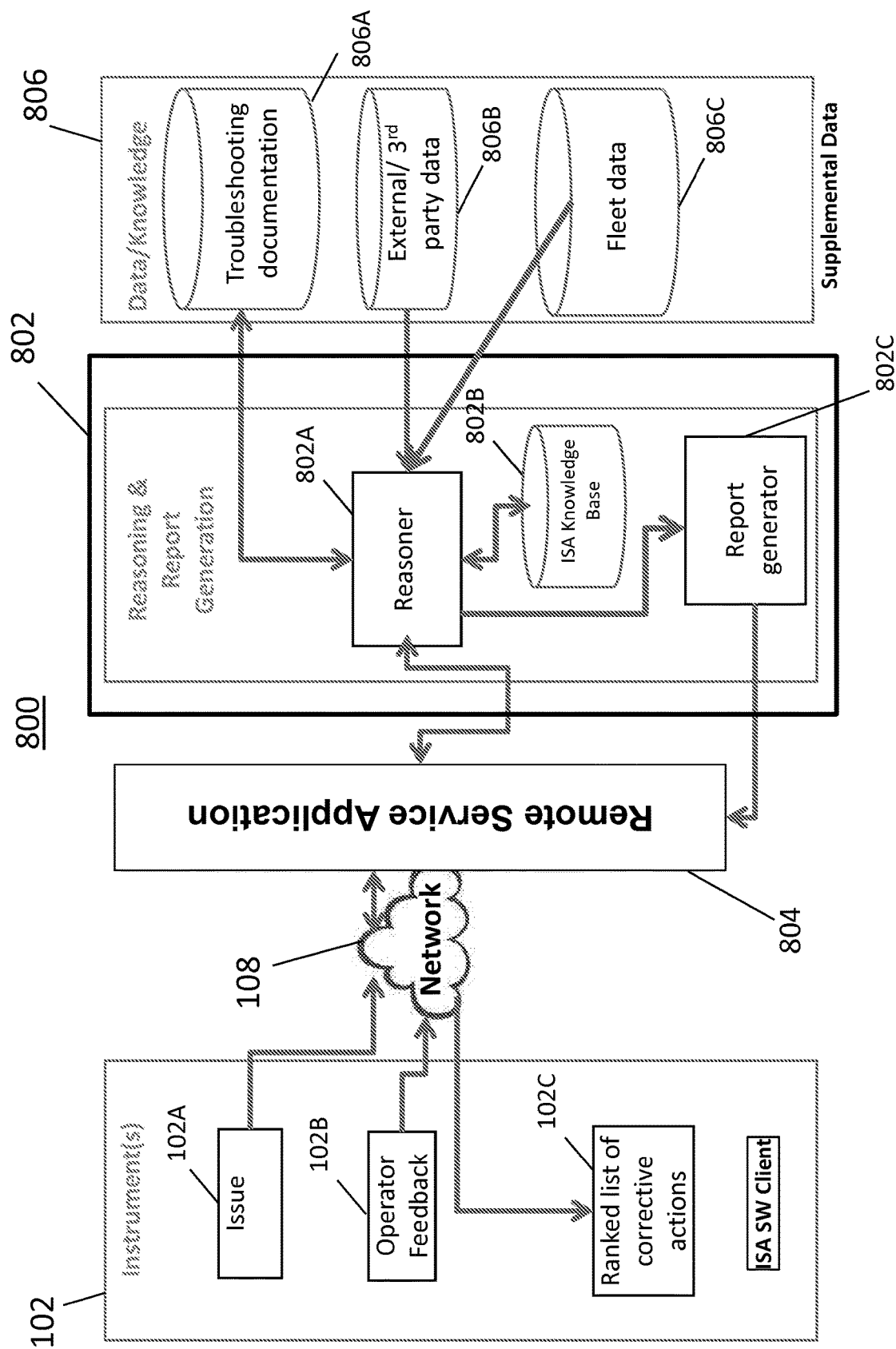
FIG. 8 is a system diagram of an exemplary ISA system configured to provide dynamic analysis for troubleshooting in vitro diagnostics instrument issues, according to some embodiments.

FIG. 8 is a system diagram of an exemplary ISA system 800 configured to provide dynamic analysis for troubleshooting in vitro diagnostics instrument issues. Similar to ISA system 100 shown at FIG. 1, the ISA system 800 may include in vitro diagnostics instruments 102. Further, each in vitro diagnostics instrument 102 in ISA system 800 may include the components of the in vitro diagnostics instruments 102 in ISA system 100. System also includes second database, ISA Knowledge Base 106. The ISA Knowledge Base 106 may be a central database in communication with each of the in vitro diagnostics instruments 102.

The second computing device in ISA system 800 is inference engine 802. As shown, in vitro diagnostics instruments 102 may include an identified issue 102A which may be provided to the inference engine 802 via network 108. In some embodiments, the description of the issue 102A may be linked to an instrument ID. Operator feedback 102B associated with the instrument and/or the issue may be provided via a remote service application 804 to the inference engine 802. The operator feedback 102B provides a description of which corrective action is associated with an issue being worked as reported by the operator of the instrument. The remote service application 804 in this case is a central service management application to dispatch customer service engineers (e.g., integrated alerts, tickets, etc.). The application 804 provides general interface functionality to facilitate communication between the in vitro diagnostics instruments 102 and the inference engine 802. A description of which corrective action associated with an issue was successful may be indicated by the operator of the instrument and an ordered (e.g., ranked) list of the corrective actions 102C may be displayed on the instrument.

The inference engine 802 may include reasoner 802A configured to determine (e.g., deduce and infer) actions from operator data across a population of in vitro diagnostics instruments 102 to add value to the ISA Knowledge Base 802B. Report generator 802C generates a report from the ISA Knowledge Base 802B which indicates "best corrective action" per issue sourced from supplemental data 806. As described above, the ISA Knowledge Base 802B is a database containing the list of issues and corrective actions for troubleshooting; it is a tool to create and maintain content is the ISA Knowledge Base editor.

The supplemental data 806 includes troubleshooting documentation 806A (e.g. cleaning procedures), external data 806B, and fleet data 806C. The troubleshooting documentation 806A provides static troubleshooting documentation (e.g., cleaning procedures, etc.). The external data 806B comprises data provided by third parties and other external sources. For example, the external data 806B may include vendor data on reagent problems, Randox reagent lots, and/or patient data. The fleet data 806C comprises data collected from instruments across a fleet (e.g. calibration data, call center data, system logs from instruments).

An example application of the rules engine is as follows: An operator cannot fix, for example, a temperature sensitive assay with the presented solution strategies. The operator's navigation path and/or the issue/event code from the instrument which resulted in accessing the ISA are stored in a system log file of the instrument. The system log file is transmitted, via, for example, an internet or other connection, to the customer service center and made available to the inference engine. Next, the operator has the possibility to select "Perform SRS Analysis" (see, e.g., the interface shown in FIG. 5).

Figure 9:
FIG. 9 shows a sample interface that may be presented while sending data, in some embodiments.
Figure 10:
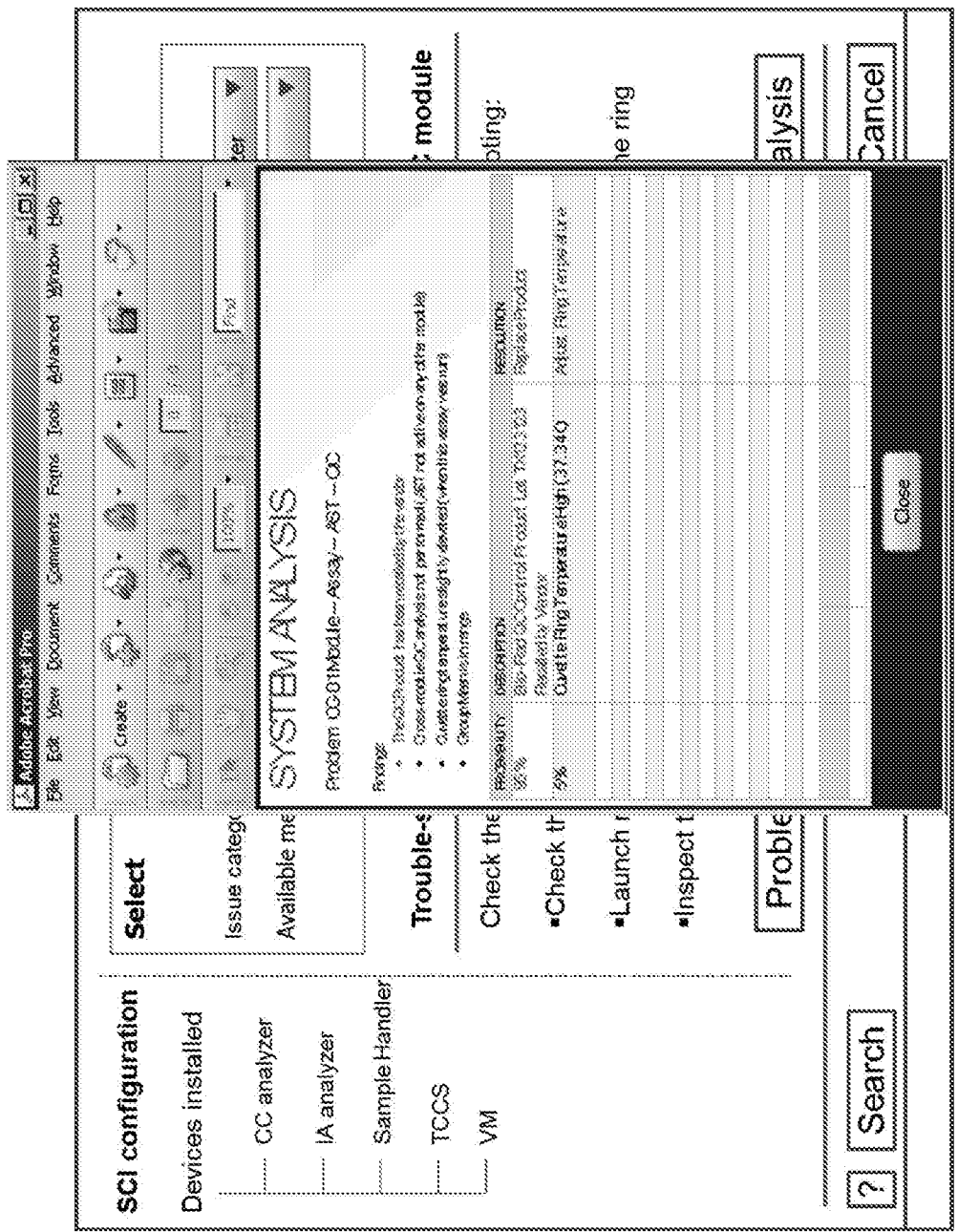
FIG. 10 illustrates an analysis report of the most successful solution strategies across a fleet of instruments, according to some embodiments.

Following initiation of the "Perform SRS Analysis" request, the ISA software client requests an on-demand report generation of solution strategies. FIG. 9 shows a sample interface that may be presented while sending data, in some embodiments. The ISA Inference Engine receives the request for an on-demand report relating to the issue/error code of the issue which could not initially be solved by the operator. Based on the event and the code, the ISA Inference Engine creates an analysis report of the most successful solution strategies across a fleet of instruments, as shown in FIG. 10. The report for the issue ID is rendered on the ISA software (SW) client. The report indicates, for the example of the issue relating to the temperature sensitive assay, the most effective way to resolve the temperature sensitive issue on a CC instrument (e.g., replace a Bio-Rad lot).

Figure 11:
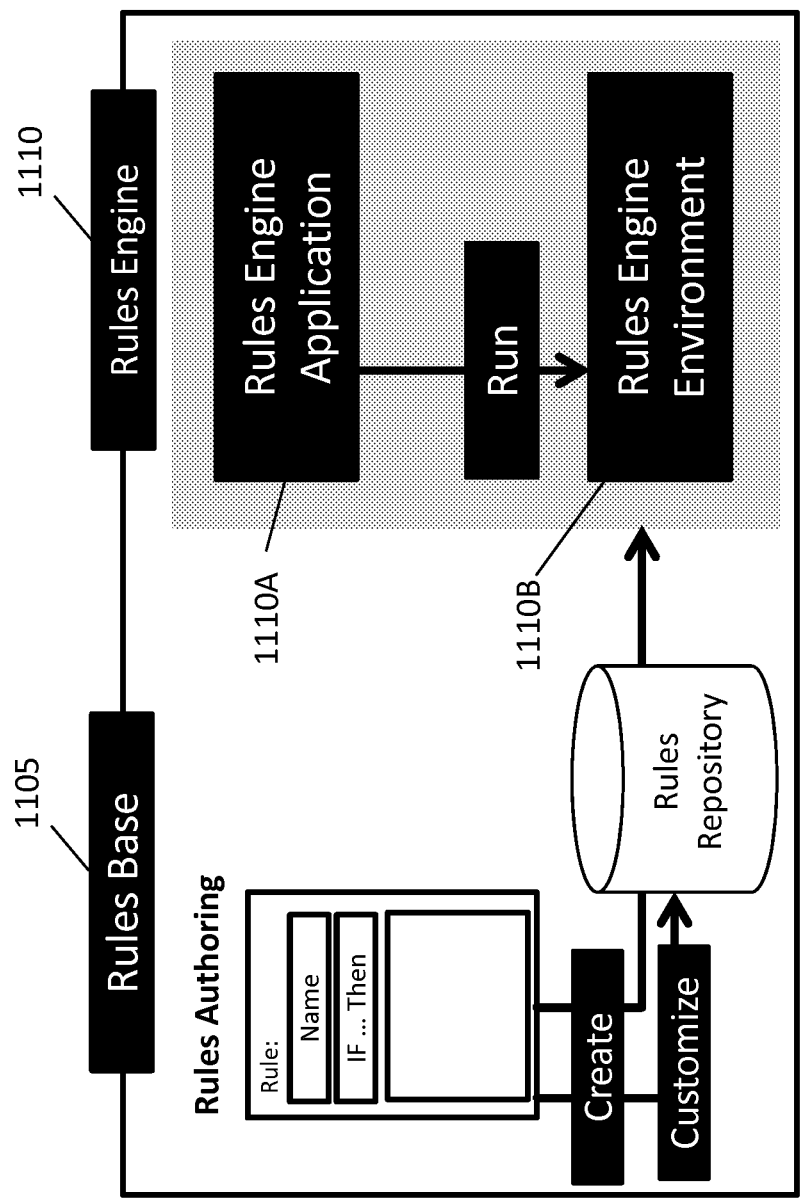
FIG. 11 shows the technical architecture of the ISA Inference Engine, according to some embodiments.

In an embodiment, the technical architecture of the ISA Inference Engine may be depicted as shown in FIG. 11. The rules base 1105 provides the tools and repository to create, customize, test, and store rules. The rules base 1105 is a central repository that contains identified issues with related solution strategies (i.e., rules). Various users, such as development engineers and customer service engineers, may access a knowledge base content editor to create and/or edit issues that are encountered, carry out a root cause analysis, and/or derive applicable solution strategies for remedying the issue. The rule can be tested for correctness of its formal description (e.g., correct syntax using a preferred or approved rules language). The rule is then stored in the rules base 1105. A customer service engineer can also load an existing rule from the rules base 1105 and then make changes. The rules authoring environment may enable multi-user access and collaboration between users; for example, to define different flows using the rules language. Additionally, each rule may be versioned and its changes tracked. Regularly or upon request, an update may be sent to instruments over a network (e.g., the Internet, an intranet, or the like).

A rules engine 1110 is used to run the rules stored in the rules base 1105. The functionality that the rules engine 1110 provides is a semi-automated or automated reasoning capability to relate issues to the best-fit solution strategies based on reported success/failure patterns across a fleet of instruments. Based on a selected rule that an operator wants to apply (e.g., find the best solution strategy for a temperature sensitive assay), the rules engine application 1110A executes the rule in the rules engine environment 1110B. The output of such a request is a list of best-fitting solution strategies per issue. Another use of executing a query is a request for the "Perform SRS Analysis" as described above. Yet another use of the ISA Inference Engine is the use to carry out a reprioritization in which solution strategies are presented to the operator on the instrument. Based on continuous collection of an operator's feedback and reasoning capability, the ISA rules base will be kept continuously updated. The local ISA knowledge or rules base (i.e., the database on a particular instrument) may be updated remotely with refreshed content.

To illustrate example application of the systems and methods described herein, two use cases are discussed below. The first use case is automatically identifying best fit corrective actions to troubleshoot an issue across a fleet of instruments. The second use case involves the semi-automatic identification of issue patterns across a fleet of instruments and the creation of additional rules. This second use case includes two variants which highlight the use of an ISA case-based reasoner and a rule-based reasoner respectively.

The pre-conditions for an automated identification of a best fit solution (aka set of corrective actions) for a specific issue across a fleet of instruments include the operator's usage of ISA (software log errors/event codes/operator's ISA path taken, success/failure of corrective actions recorded) for subsequent analysis (e.g., as provided via ISA SW client shown in FIG. 8). Additionally, a statistically significant number of operator's ISA usage path as well as success and failure data per issue should be available to do an analysis of a best solution fit.

The workflow for the automated identification of a best fit solution is as follows. First, the operator's error/event code, operator's ISA path, success/failure of issue resolved over a fleet of instruments is transmitted over network to the Remote Service Application and stored. Next, a best fit solution analysis is performed and the per-issue the success/failure rates are evaluated creates a relative success score per corrective action is created. Once the relative success score of a corrective action has changed (to the better more useful to the operator), the priority of the corrective action gets updated within the current list of applicable corrective actions and stored in the ISA Knowledge Base. The local ISA Knowledge Base of the instrument is regularly updated (e.g., at a pre-determined frequency) via remote software updates.

Later, after the operator has tried proposed corrective actions without success, the ISA SW client activates Perform SRS Analysis button and the operator hits the SRS Analysis button (see FIG. 9, "Perform SRS Analysis" button). Next, the system Instrument Manager requests an analysis report from the Remote Service Application (see FIG. 8). Then, the Remote Service Application triggers the report engine to create a report using the issue ID which could not be resolved by the operator prior. The Remote Service Application transmits analysis report (for issue ID) to the instrument and the ISA SW client renders the analysis report for viewing by the operator in the lab with a list of the prioritized most successful corrective actions used across a fleet of instruments (see, e.g., FIG. 10). Then, the operator carries out corrective actions to fix the instrument. The operator reports which corrective actions were successful (see FIG. 6). The System Instrument Manager transmits the data to the Remote Service Application.

Figure 12:
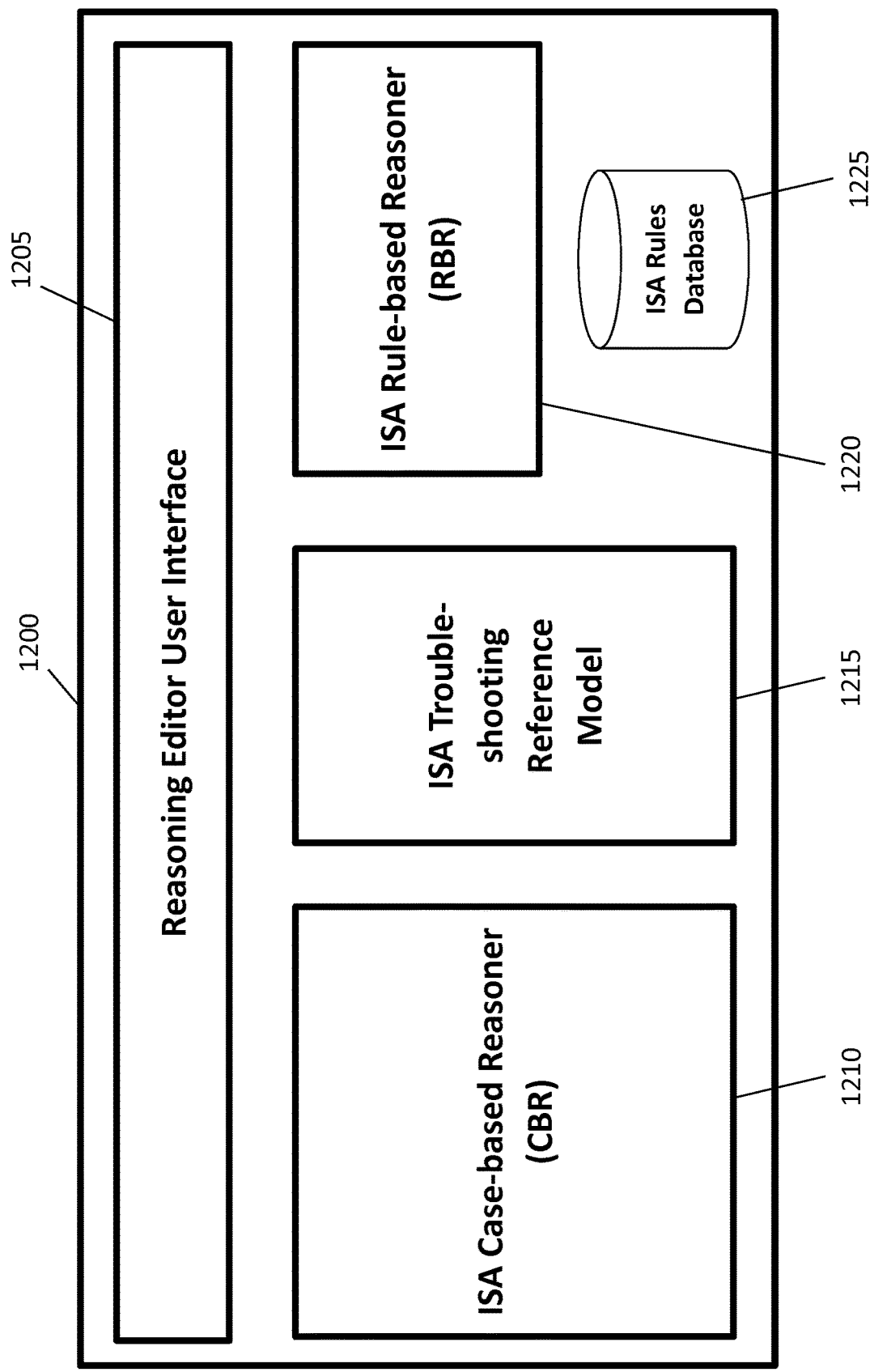
FIG. 12 illustrates the main components of an ISA Expert System as may be applied, according to some embodiments.

For the second use case, an ISA Expert System is developed to semi-automatically identify issue patterns across a fleet of instruments and create additional rules (e.g., issues, corrective actions). FIG. 12 illustrates the main components of an ISA Expert System 1200 as may be applied in the second use case, according to some embodiments. The Reasoning Editor User Interface 1205 provides a way for a content developer to access the functionality of the case-based and rule based reasoning engines. The ISA case-based reasoned reuses similar cases to understand a problem and suggests a solution based on prior documented experience. The ISA Rules-based Reasoner 1220 is used to derive new generally valid rules for the ISA Knowledge Base with the goal to connect an explicit issue to specific corrective actions (to achieve an event-code driven ISA behavior). The ISA Rules Database 1225 provides data storage for qualified ISA rules to assess issues. Finally, the ISA Troubleshooting Reference Model 1215 provides a representation of troubleshooting body of knowledge in the form of a standard model which can be used to derive general rules from.

As one example application of the ISA Expert System 1200, consider a case-based reasoner (CBR). ISA content generation is highly manual, though an initial knowledge base editor is available for creating solid source for feeding an expert system application. CBR is a way to automate identification, creation and maintenance of issues, as well as corrective actions. CBR applies "reasoning" capability to avoid creation of redundant ISA Knowledge Base entries. Additionally, a document customer service engineer's expert knowledge may be applied to make it searchable, assessable and comparable. The pre-requisite for using the CBR is an existing ISA Knowledge Base from prior products that can be used as a starter to define a troubleshooting reference model as well as derive a set of cases for the case database. More specifically, the assumption is that there is a documented set of cases (e.g., including problem, corrective actions, and feedback from operator on success/failure documented).

The base principle with CBR is that, in the reasoning process, CBR reuses similar old cases to understand the problem specification, and suggest corrective actions. The defined reasoning techniques include retrieve, reuse, revise, and retain. The retrieve technique identifies, descriptive characteristics of a new problem (e.g., relevant for the CBR; omitting characteristics non-relevant), matches the new problem to existing case, selects best matched case from a collection of similar cases (i.e., match of similarity profile). The reuse technique selects a case (approximating or matching) that can be compared to new specific characteristics. New corrective actions can be worked out either by reuse or adapting the ones present. The revise reasoning technique may be used to evaluate how closely corrective actions for an issue (e.g., either through simulation or a customer service engineering expert). CBR learns through success/failure reported and through updated corrective actions by a human expert. Finally, the retain technique may be used to preserve new issue and corrective action that have been confirmed to work or not work.

To illustrate a workflow for the CBR approach, consider a scenario where the Remote Service Application (see, e.g., FIG. 8) creates an alert on unresolved issue (e.g., stemming from an operator reporting a failure to resolve an issue with current set of defined issues and associated corrective actions in the ISA Knowledge Base). The Remote Service Application notifies customer service engineer via an alert.

Figure 13:
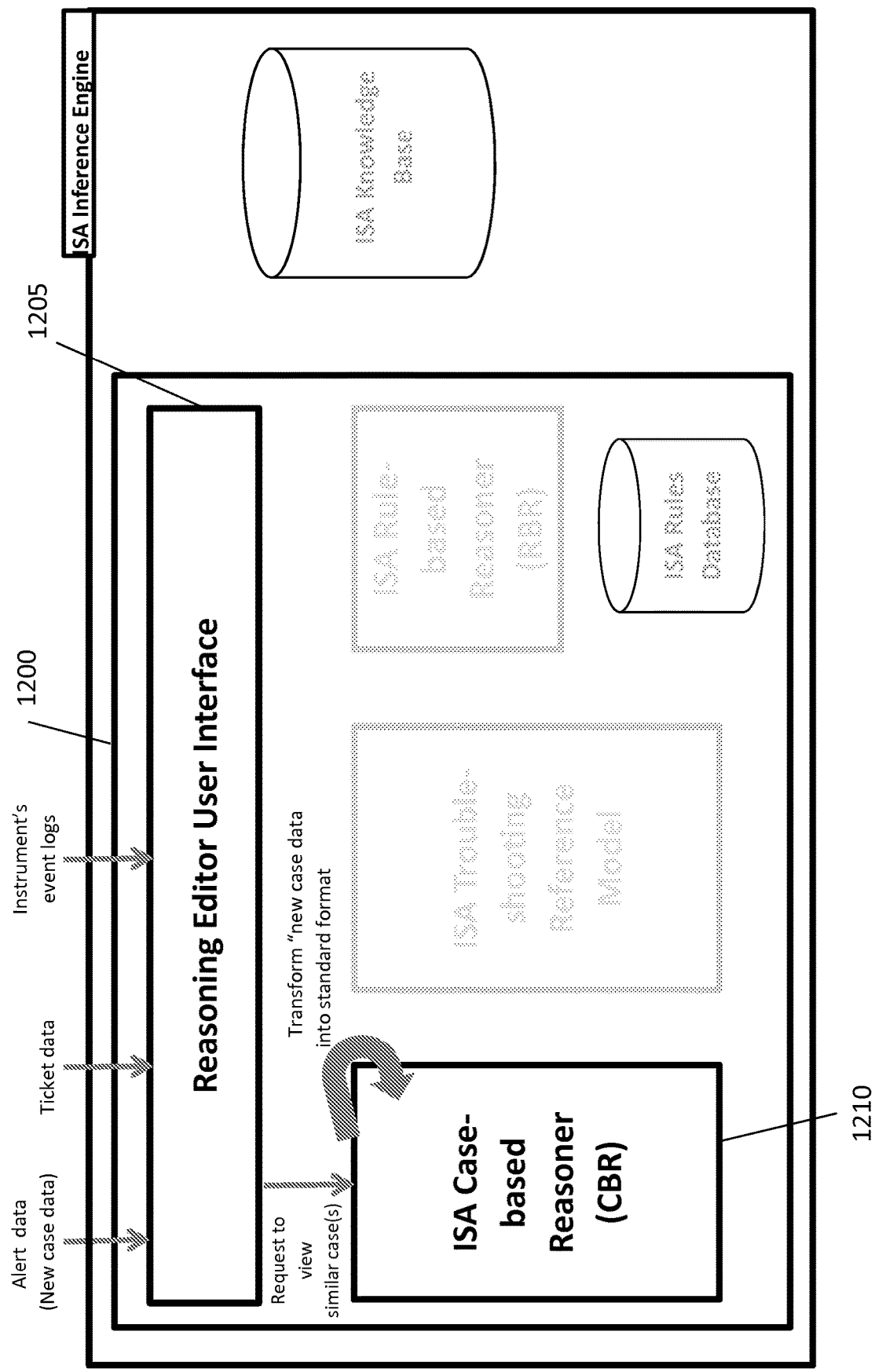
FIG. 13 illustrates a first set of steps in a Case-Based Reasoner (CBR) example that may be implemented using some embodiments.

FIG. 13 illustrates the next steps in the CBR example. The customer service engineer reviews/interpret list of potential inputs via the Reasoning Editor User Interface 1205. These inputs may include, for example, ISA operator feedback, success/failure on corrective action(s); condition-based maintenance data/properties; alert/alarm of an unresolved issue on an instrument "temperature sensitive assay on a clinical chemistry analyzer;" instrument event logs; non-event based operator searches; and ticket data on instrument issue from CRM systems. The customer service engineer requests to view similar case(s) via the Reasoning Editor User Interface 1205. The ISA CBR 1210 transforms "new case data" into standard format.

Figure 14:
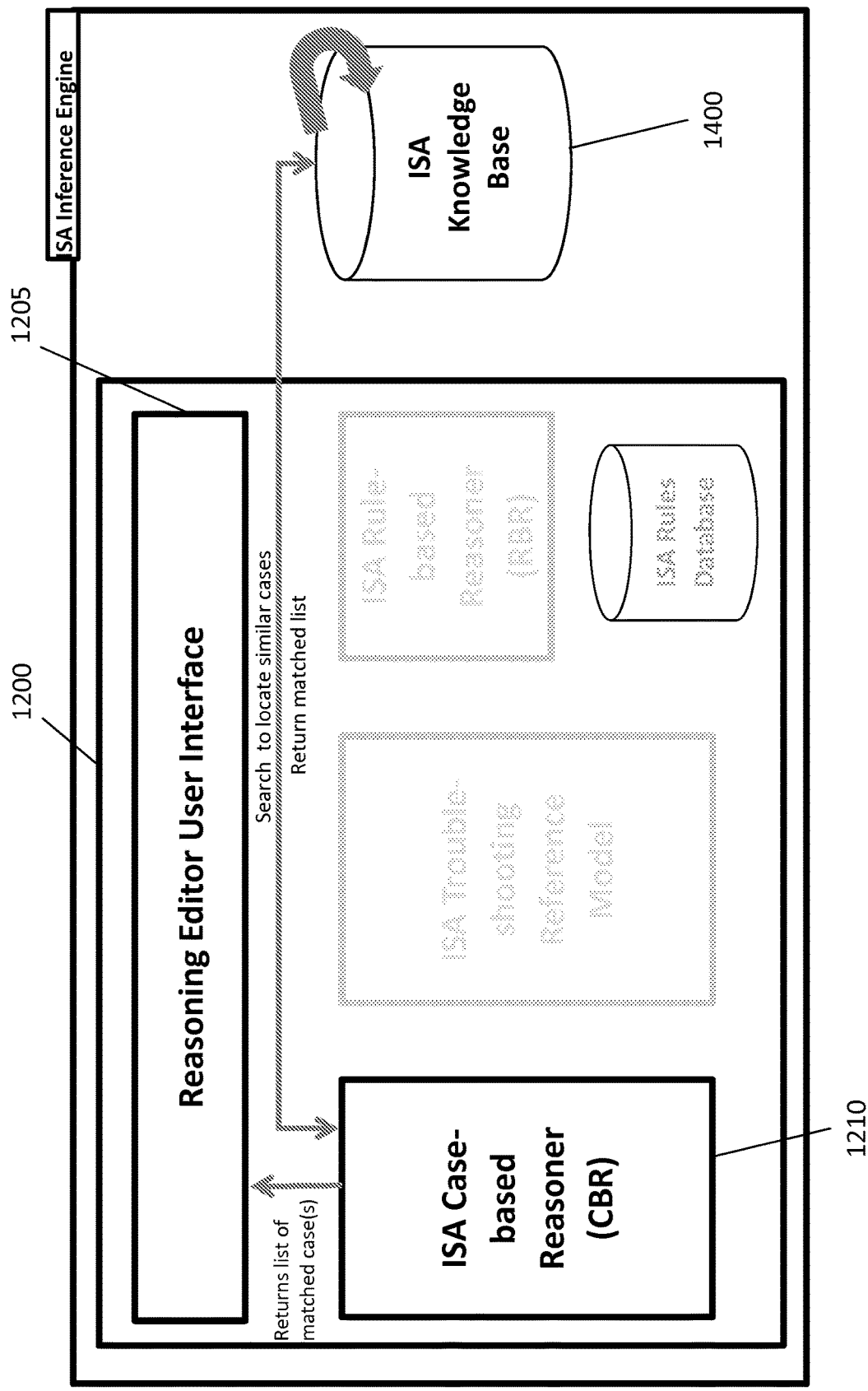
FIG. 14 illustrates a second set of steps in the CBR example that may be implemented using some embodiments.

The customer service engineer uses the Reasoning Editor User Interface 1205 to trigger a search against the ISA Knowledge Base to locate similar case(s). For example, assume that issue to consider is "temperature sensitive assay on Clinical Chemistry analyzer" which could not be resolved. FIG. 14 provides an illustration of how the ISA Expert System 1200 processes this information. Specifically, the ISA CBR 1210 queries the ISA Knowledge Base 1400 for existing or similar cases "temperature sensitive assay on Clinical Chemistry analyzer." Next, the ISA CBR 1210 returns list of matched case(s) to the Reasoning Editor User Interface 1205.

Figure 15:
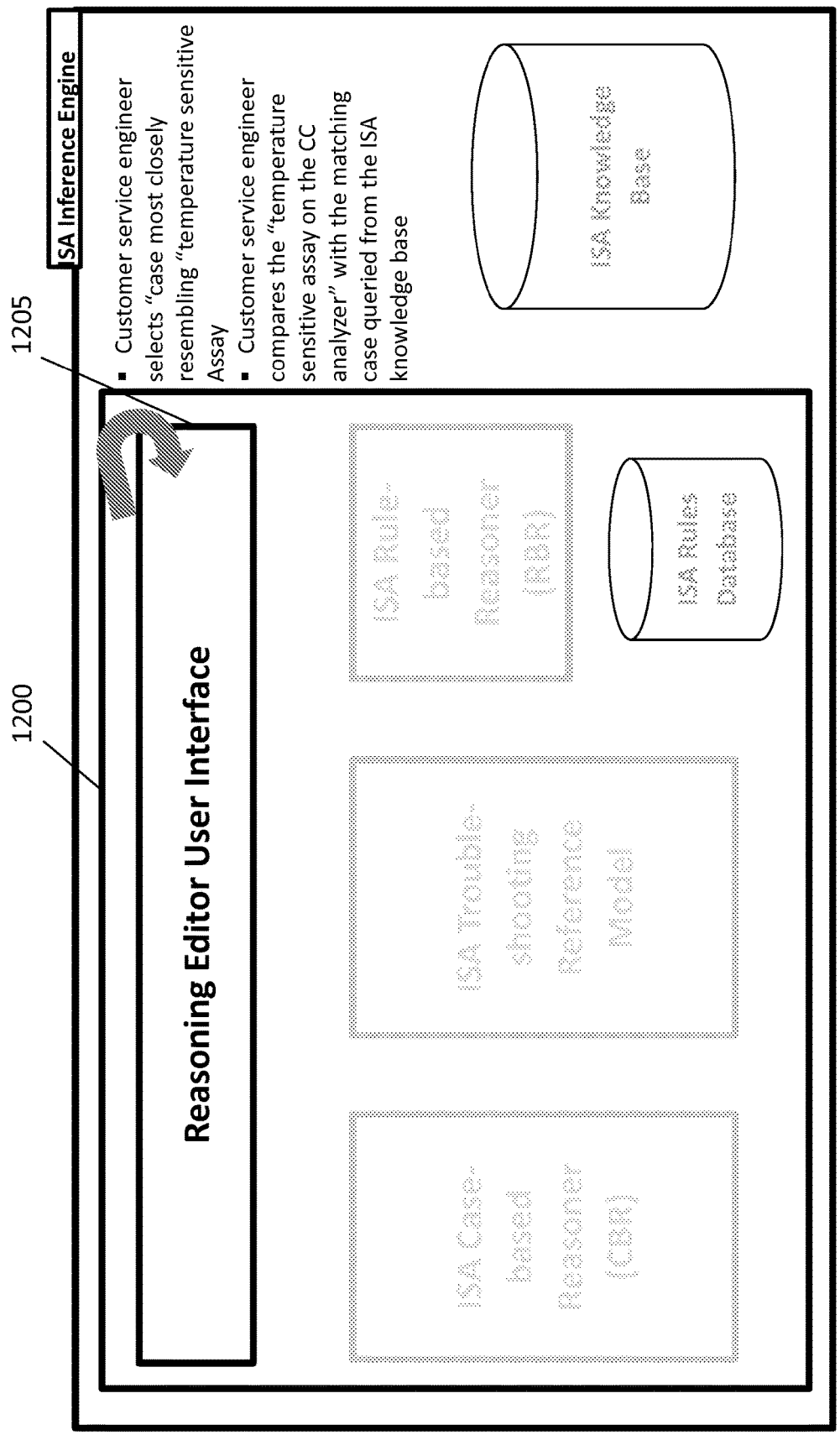
FIG. 15 illustrates a third set of steps in the CBR example that may be implemented using some embodiments.

FIG. 15 depicts the next two steps in the CBR example. The customer service engineer uses the Reasoning Editor User Interface 1205 to select the case most closely resembling "temperature sensitive assay." The customer service engineer then compares the "temperature sensitive assay on the CC analyzer" with the matching case queried from the case database.

Figure 16:
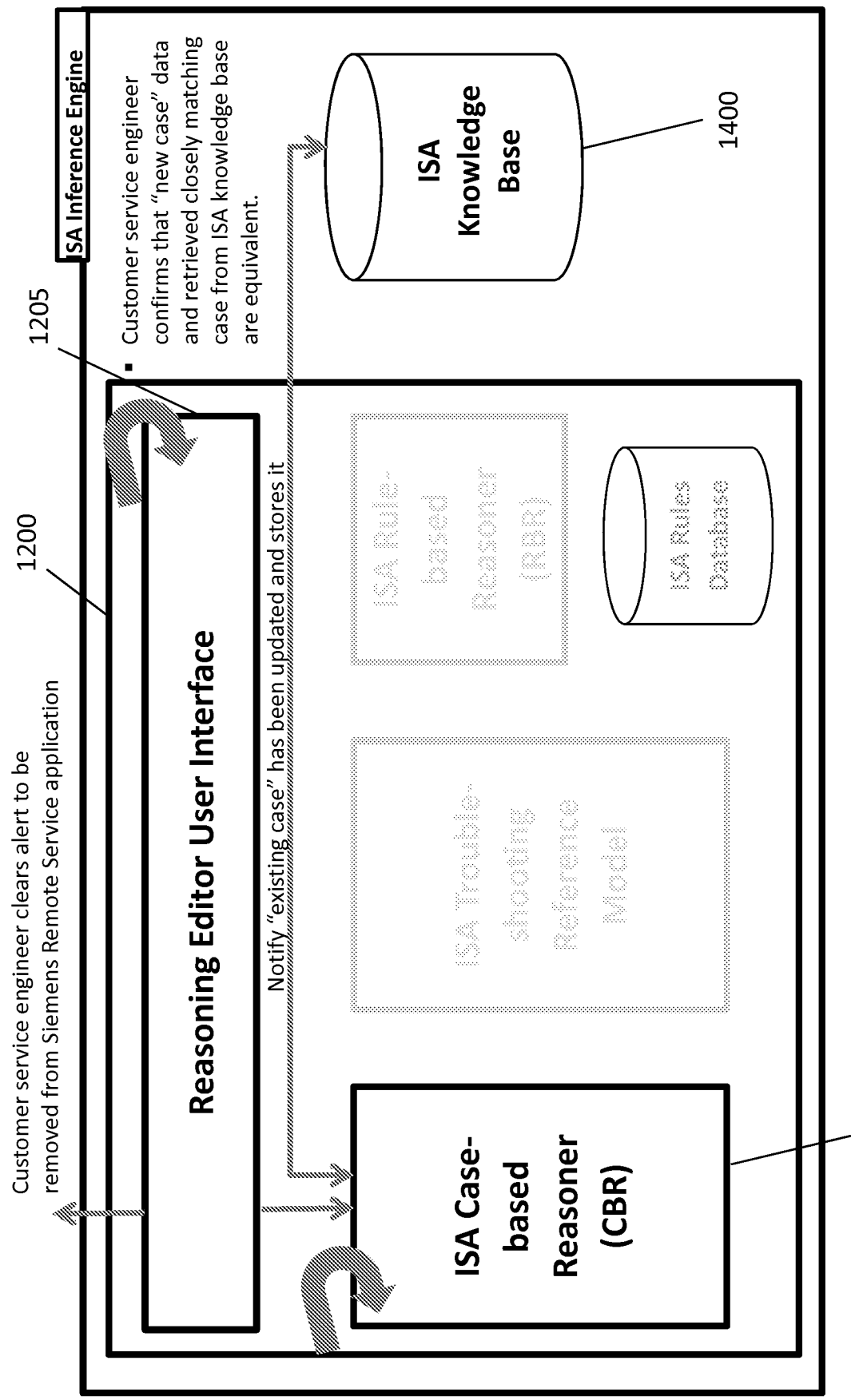
FIG. 16 illustrates a fourth set of steps in the CBR example that may be implemented using some embodiments.

FIG. 16 shows the remaining steps in the CBR example. If there are differences between the "temperature sensitive assay on the CC analyzer" and the matching case queried from the case database, the customer service engineer makes annotations (if any differences) via the Reasoning Editor User Interface 1205 and saves the case "temperature sensitive assay on the CC analyzer" as a new case. If there are no significant differences, the customer service engineer notates that both cases (existing and new) are applicable also for "temperature sensitive assay on the CC analyzer." The case history is updated to apply to the temperature sensitive assay on the CC analyzer" as well. The ISA Knowledge Base 1400 notifies the ISA CBR 1210 that case (updated or new) has been stored. Finally, the customer service engineer clears alert to be removed from the Remote Service Application.

Figure 17:
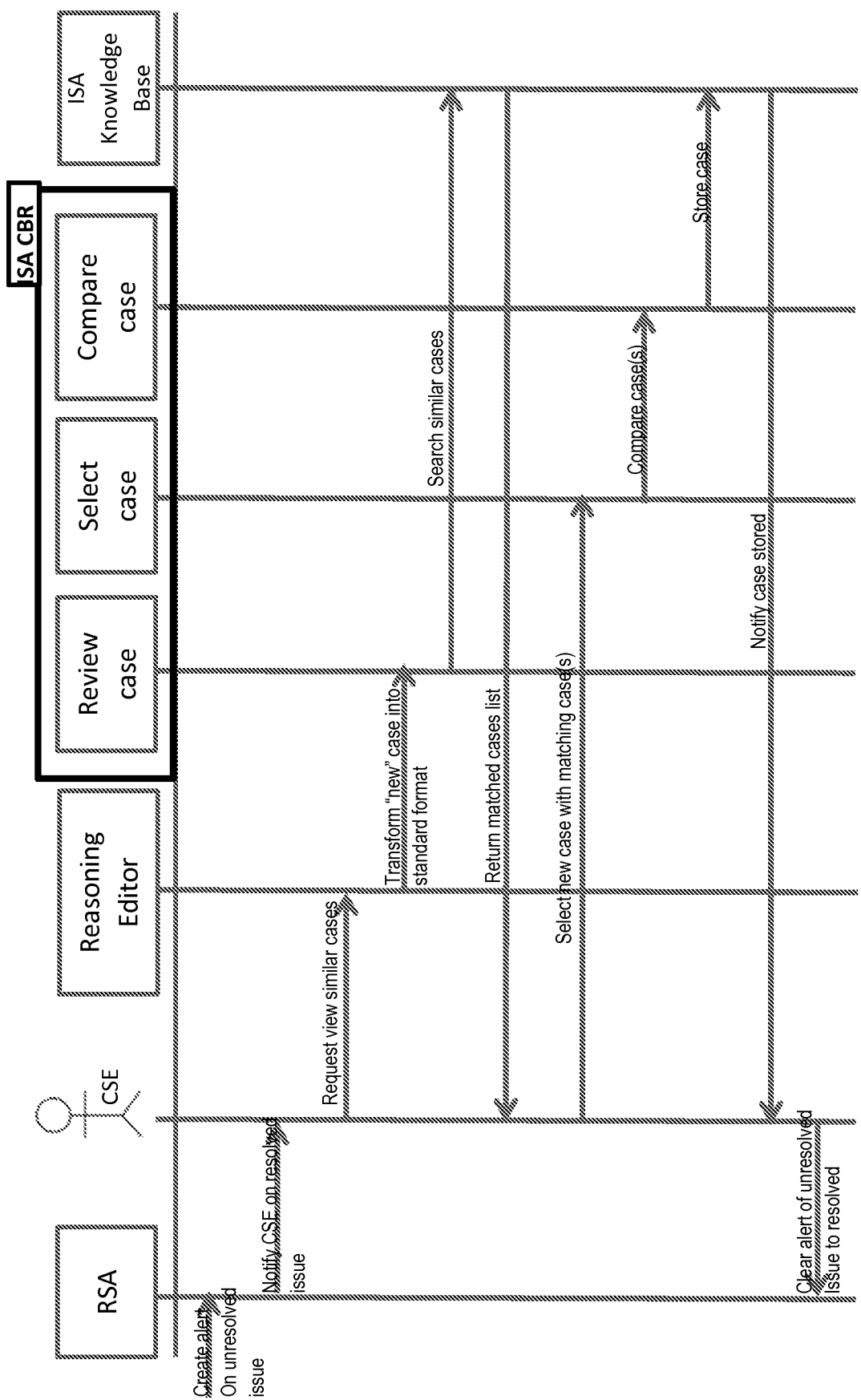
FIG. 17 provides a message sequence diagram for the CBR example discussed with reference to FIGS. 13-16.

FIG. 17 provides a message sequence diagram for the CBR sample workflow discussed above.

As a second example application of the ISA Expert System 1200, consider a Rule-based Reasoner (RBR) 1220. Not every issue that is encountered is documented as an existing case in the ISA Knowledge Base (i.e., it is limited to no reuse). When modelled in an ISA Troubleshooting Reference Model 1215, the existing ISA Knowledge Base (i.e., existing cases) can help to derive more general rules—explicit knowledge to make it accessible with an event code with detailed corrective actions. The pre-requisite for the ISA RBR 1220 is that the ISA Troubleshooting Reference Model 1215 needs to be modelled in graph structure so it can be traversed using forward-chaining or backward chaining reasoning algorithms (formal reasoning mechanisms). Additionally, the existing content of ISA Knowledge Base (source material of issues and its associated corrective actions) needs to be mapped into the ISA Troubleshooting Reference Model 1215.

The base principle of the ISA RBR 1220 is to represent troubleshooting knowledge with set of rules and suggest corrective actions derived from rule-based reasoning. For example, these rules may be specified in the following format: "If <condition(s) for issue are true> then <corrective actions>." There are types of rule-based reasoning applied in this use case: forward chaining and backward chaining. With forward chaining, once a problem description for the troubleshooting issue (and a set of corrective actions) has been provided, a search is carried out comparing existing rules against the available set of rules in rules database. Conversely, with backward chaining, once an issue description (and a set of corrective actions) has been provided, a search is carried out using the corrective actions which are stated in a rule. Note that this technique might not be applicable if corrective actions are not available.

Figure 18:
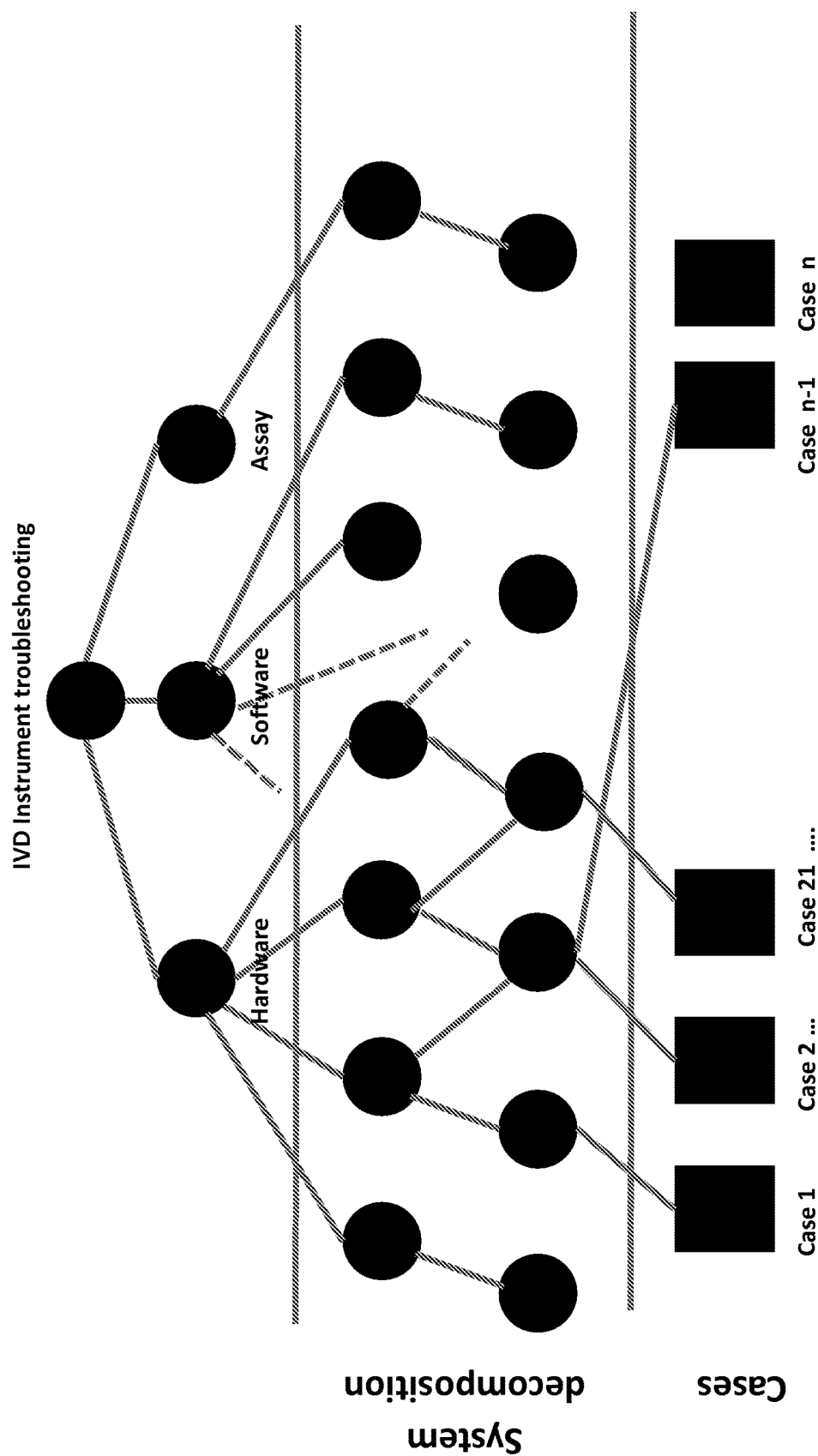
FIG. 18 provides a scheme of an ISA Troubleshooting Reference Model that may be applied in some embodiments.

FIG. 18 provides a scheme of an ISA Troubleshooting Reference Model that may be applied in the example of the RBR use case. In this illustration, troubleshooting knowledge is represented in a graph structure with each underlying concept (top-down decomposition of issue) being a node and, to each node, links of corrective actions are attached. The generic concept is troubleshooting and the general domain concept is IVD instrument troubleshooting. Due to a graph structure, there are defined pathways between concepts (top-down decomposed) and relationships with other concepts (issues). Cases can be also mapped/linked to the troubleshooting reference model. The ISA Troubleshooting Reference Model shown in FIG. 18 is based on the following pattern. First, the root is IVD Instrument Troubleshooting. The decomposition from root is hardware, software, and assay. The generic domain space is a system decomposition of IVD instrument entities. Finally, the leaves of the graph shown in FIG. 18 are attached to specific known cases of the ISA Knowledge Base.

The key functionalities of an ISA Expert System utilized by a RBR Reasoner are an ISA Rules Database, an ISA Rules-based Reasoner, and the Reasoning Editor UI. With the ISA Rules Database, rules are expressed in natural language constructs (e.g., "if <condition(s) for issue are true> then <corrective actions>"). One rule links the issue to the corrective actions and a set of rules express the customer service knowledge to be exploited. The ISA Rule-Based Reasoner is designed to produce reasoning on rules and formulated by customer service engineers. Additionally, the reasoned provides a probabilistic answer back to the customer service engineer. The Reasoning Editor UI provides functionality such as a rules language; rule authoring & testing (for ISA troubleshooting reference model); rules tracking and version control (e.g., monitoring of changes of rules over time and managing multi-user access; collaboration in use of rule repository (e.g., reuse of existing rules, flows and models); simulation of rule engine runs (i.e., load, assert/retract and perform inference) and analysis and report generation (e.g., the operator queries for specific issue to solve).

FIGS. 19-24B show a sample workflow for RBR approach. In this example, the clinical chemistry analyzer has a series of tests to do. However, one hour after loading the sample tube for testing, no test results were reported. The goal then is to determine what happened. The Remote Service Application (see FIG. 8) creates an alert on unresolved issue, indicating that the Clinical Chemistry analyzer has not delivered a result after one hour. An alert is generated on the instrument and sent to the Remote Service Application, indicating that operator has used the Intelligent Service Assistant SW client unsuccessfully. The Remote Service Application notifies customer service engineer via an alert. The customer service engineer reviews/interprets a list of potential inputs such as an alert/alarm of an unresolved issue on an instrument (e.g., "no test result on Clinical Chemistry analyzer delivered after 1 hour"); instrument event logs; non-event based operator searches; and ticket data on instrument issue from CRM systems.

Figure 19:
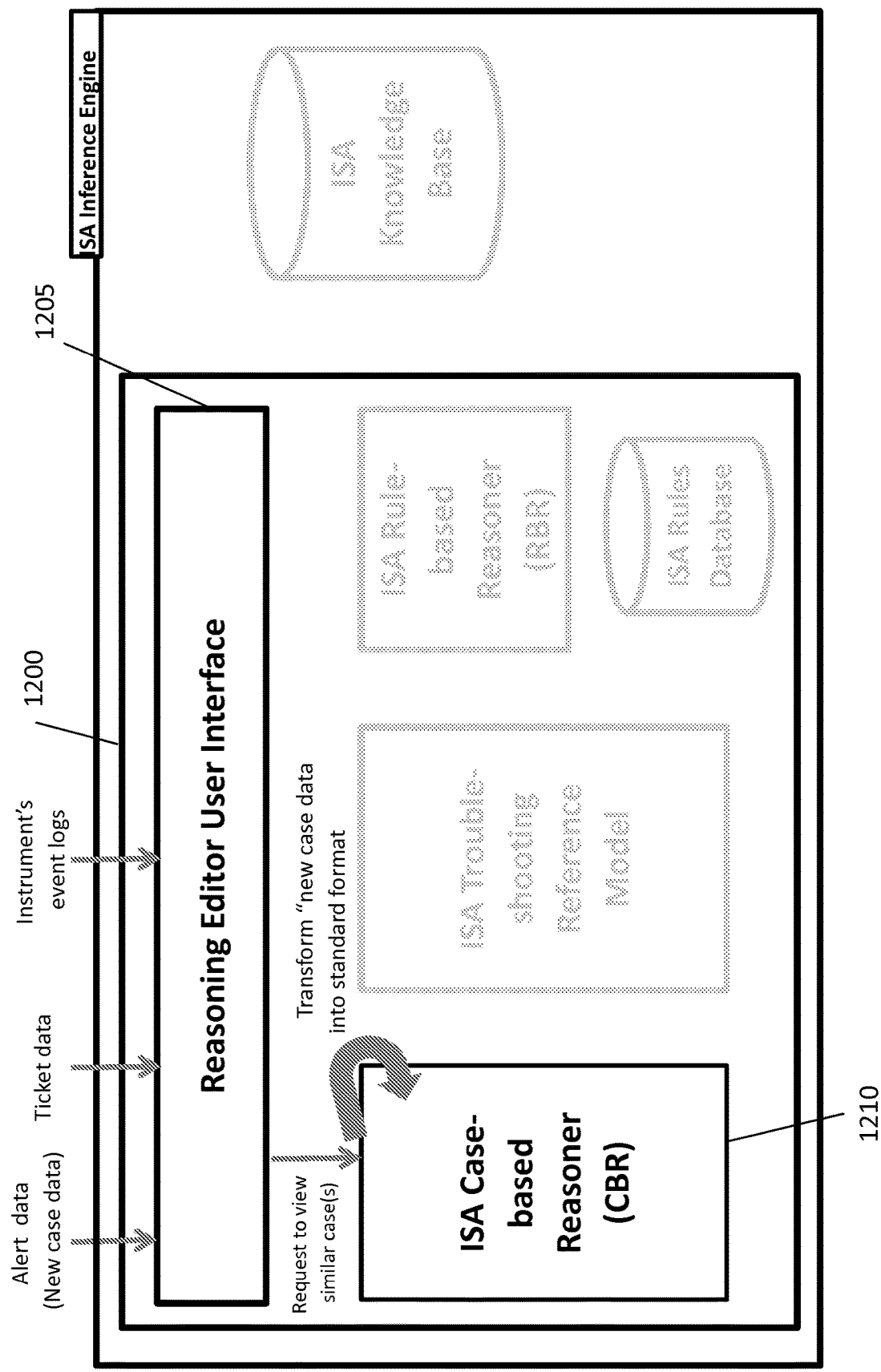
FIG. 19 illustrates a first set of steps in a Rules-Based Reasoner (RBR) example that may be implemented using some embodiments.

FIG. 19 illustrates the next steps in the RBR sample workflow. A customer service engineer requests to view similar case(s) via the Reasoning Editor User Interface 1205. Then, ISA CBR 1210 transforms "new case data—no test result after 1 hour on Clinical Chemistry analyzer" into the standard format.

Figure 20:
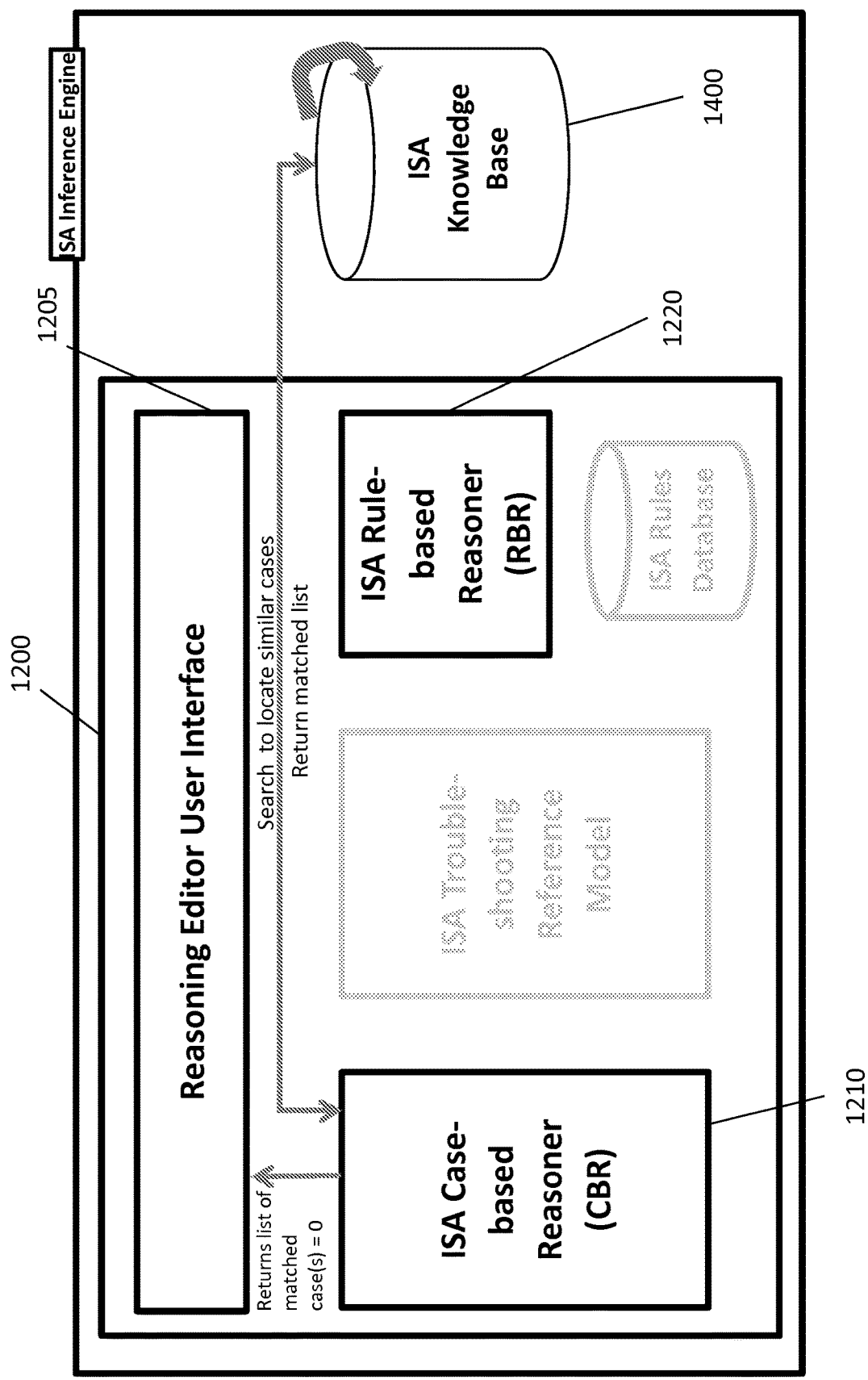
FIG. 20 illustrates a second set of steps in the RBR example that may be implemented using some embodiments.

As shown in the illustration of FIG. 20, a customer service engineer triggers a search against the ISA Knowledge Base 1400 to locate similar case(s). Assume issue to consider is "no test result after 1 hour on Clinical Chemistry analyzer" which could not be resolved. The ISA CBR 1210 queries the ISA knowledge database for "no test result after 1 hour on Clinical Chemistry analyzer." The ISA CBR 1210 returns list of matched case(s) to Reasoning Editor User Interface 1205 indicating that no cases were found for "no test result after 1 hour on Clinical Chemistry analyzer." Then, the customer service engineer requests processing of "no test result after 1 hour on Clinical Chemistry analyzer" via the Reasoning Editor User Interface 1205 and transfers to ISA RBR 1220 to transform it into a rule format.

Figure 21:
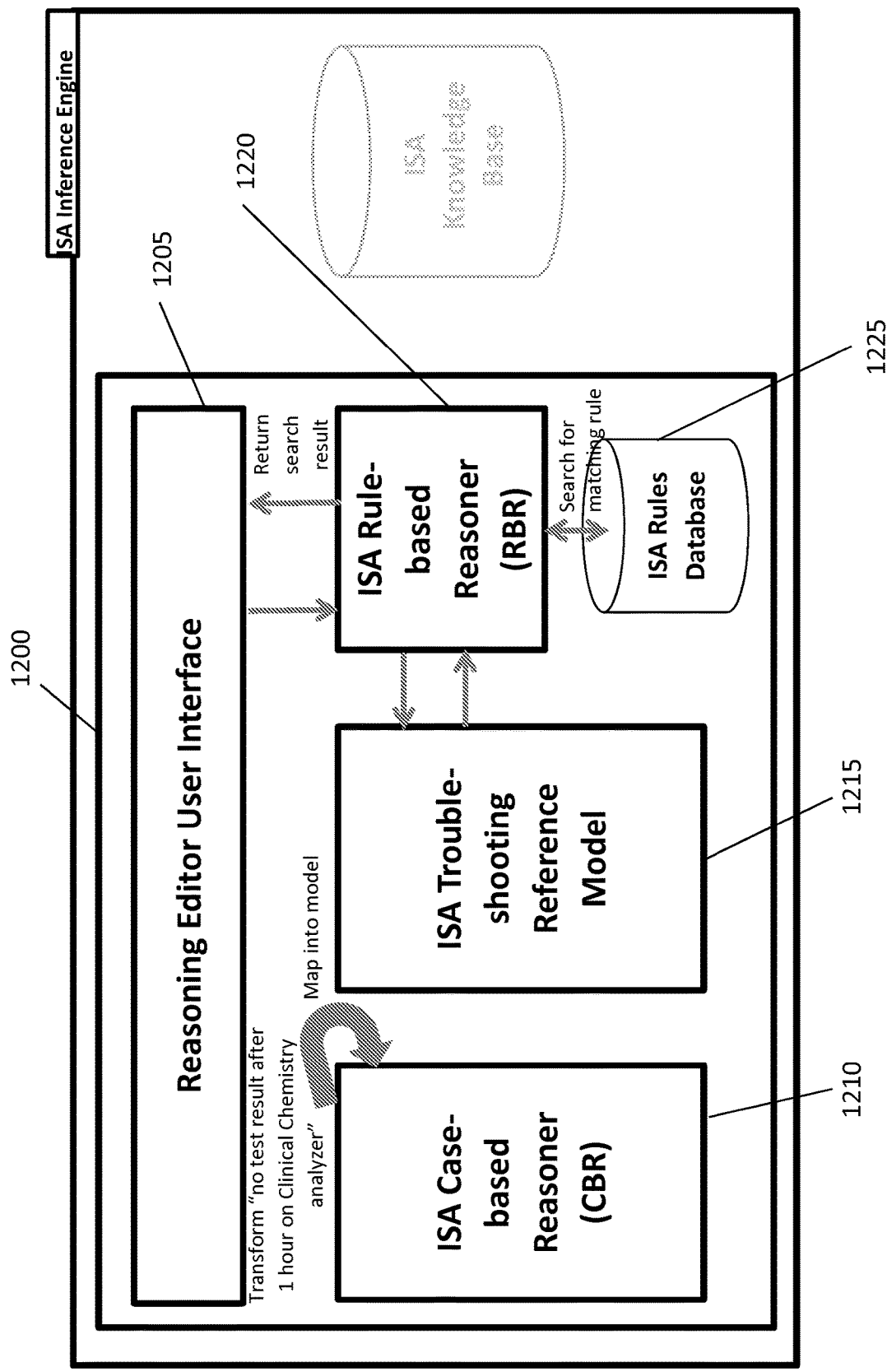
FIG. 21 illustrates a third set of steps in the RBR example that may be implemented using some embodiments.

FIG. 21 depicts the next steps in the RBR workflow for this example use case. The ISA RBR 1220 transforms "no test result after 1 hour on Clinical Chemistry analyzer" into rules format (map into model). ISA RBR 1220 searches the ISA Rules Database 1225 for applicable rules matching the "no test result after 1 hour on Clinical Chemistry analyzer" context. The ISA Rules Database 1225 returns result of applicable rules to the Reasoning Editor User Interface 1205 after testing the rules with the context "no test result after 1 hour on Clinical Chemistry analyzer". The rule extracted may be represented as shown in pseudo-code presented in FIG. 22.

Figure 23:
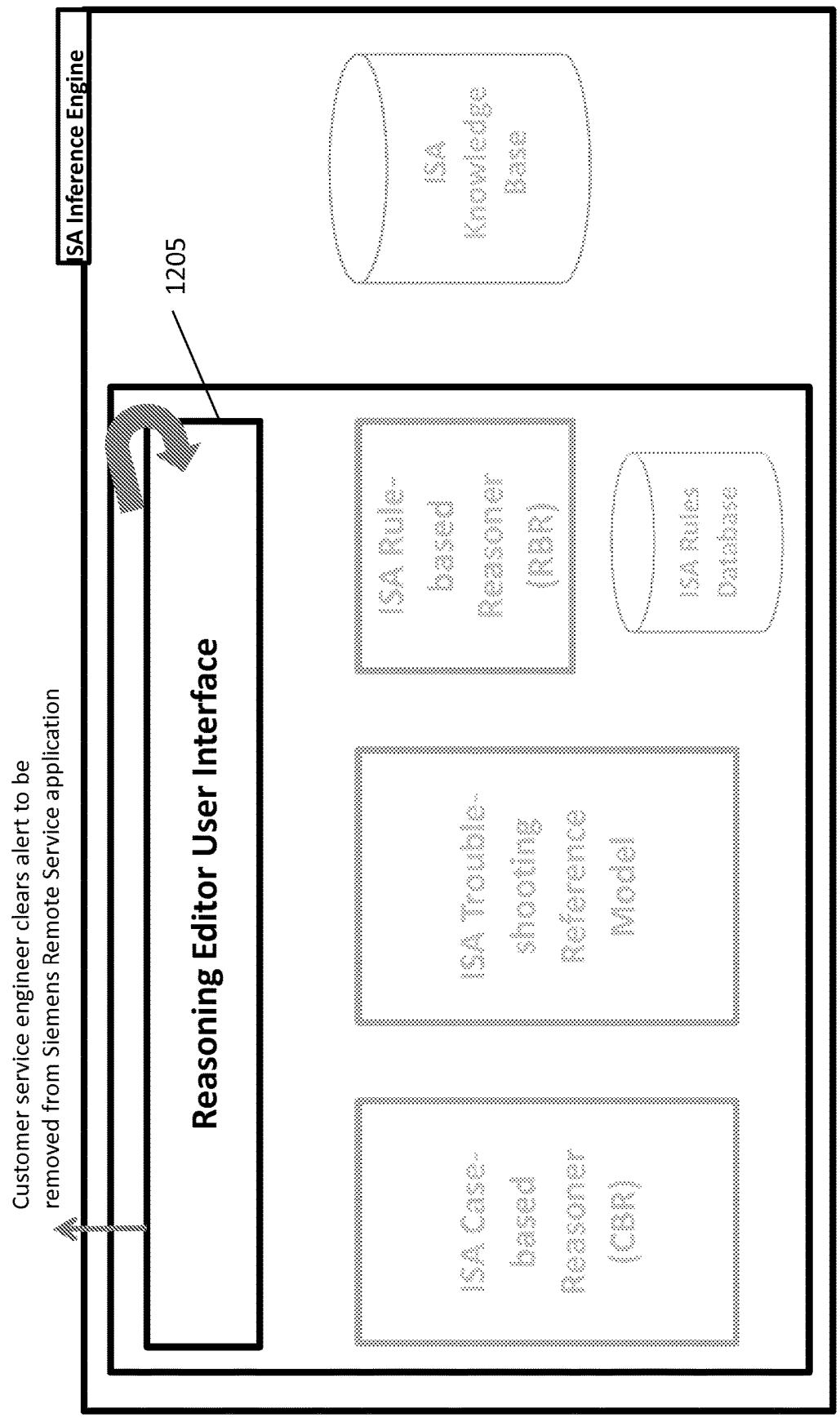
FIG. 23 illustrates a fifth set of steps in the RBR example that may be implemented using some embodiments.

FIG. 23 shows the final steps in the RBR workflow for the example use case. The customer service engineer communicates to the operator of the CC analyzer on how to carry out the fix of the Quality Control failure (offline). The customer Service Engineer clears alert to be removed from Remote Service Application via the Reasoning Editor User Interface 1205. Finally, the Remote Service Application clears alert "no test result after 1 hour on Clinical Chemistry analyzer".

Figure 24A:
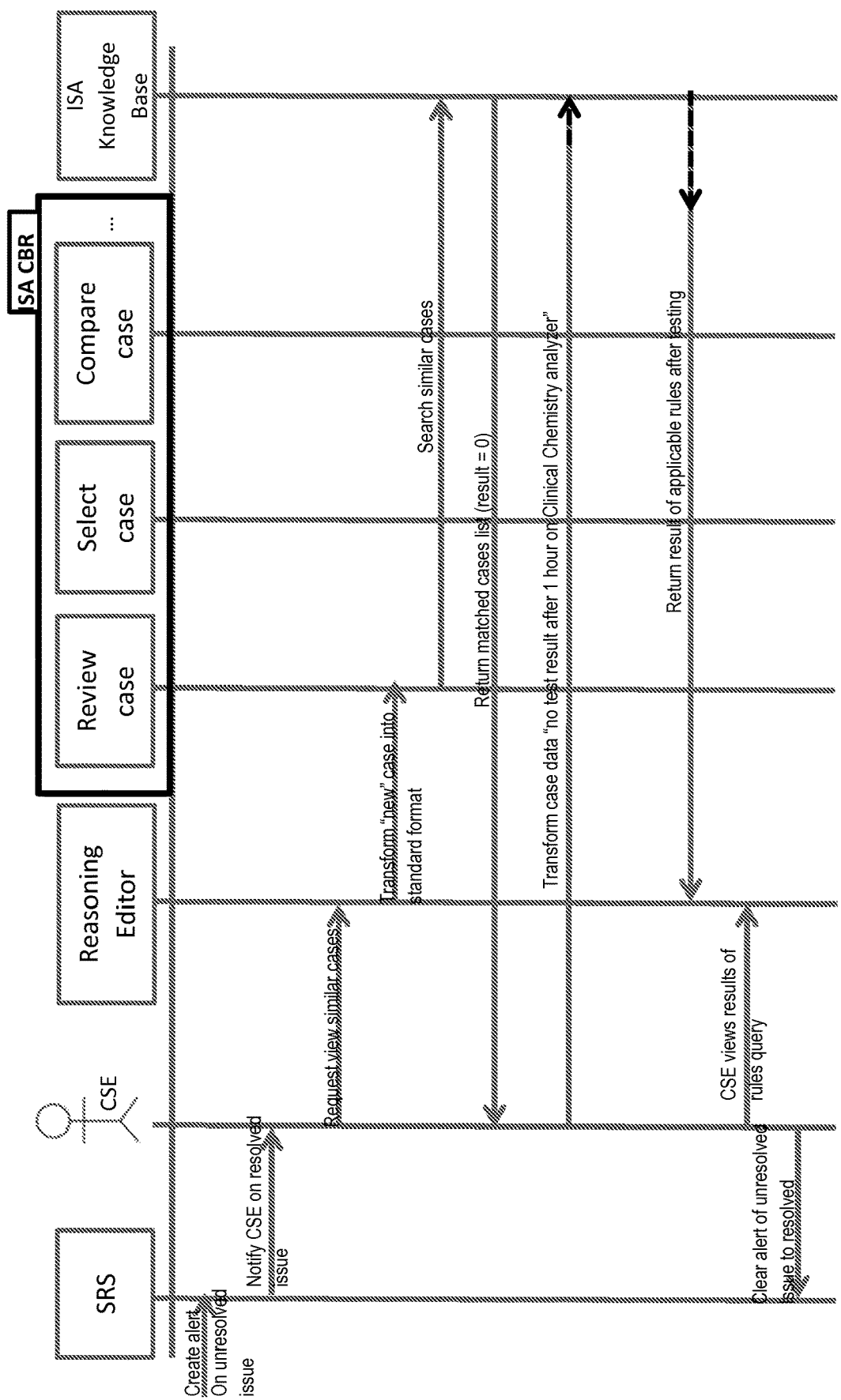
FIG. 24A shows a first portion message sequence diagrams for the RBR example, discussed with reference to FIGS. 19-22.
Figure 24B:
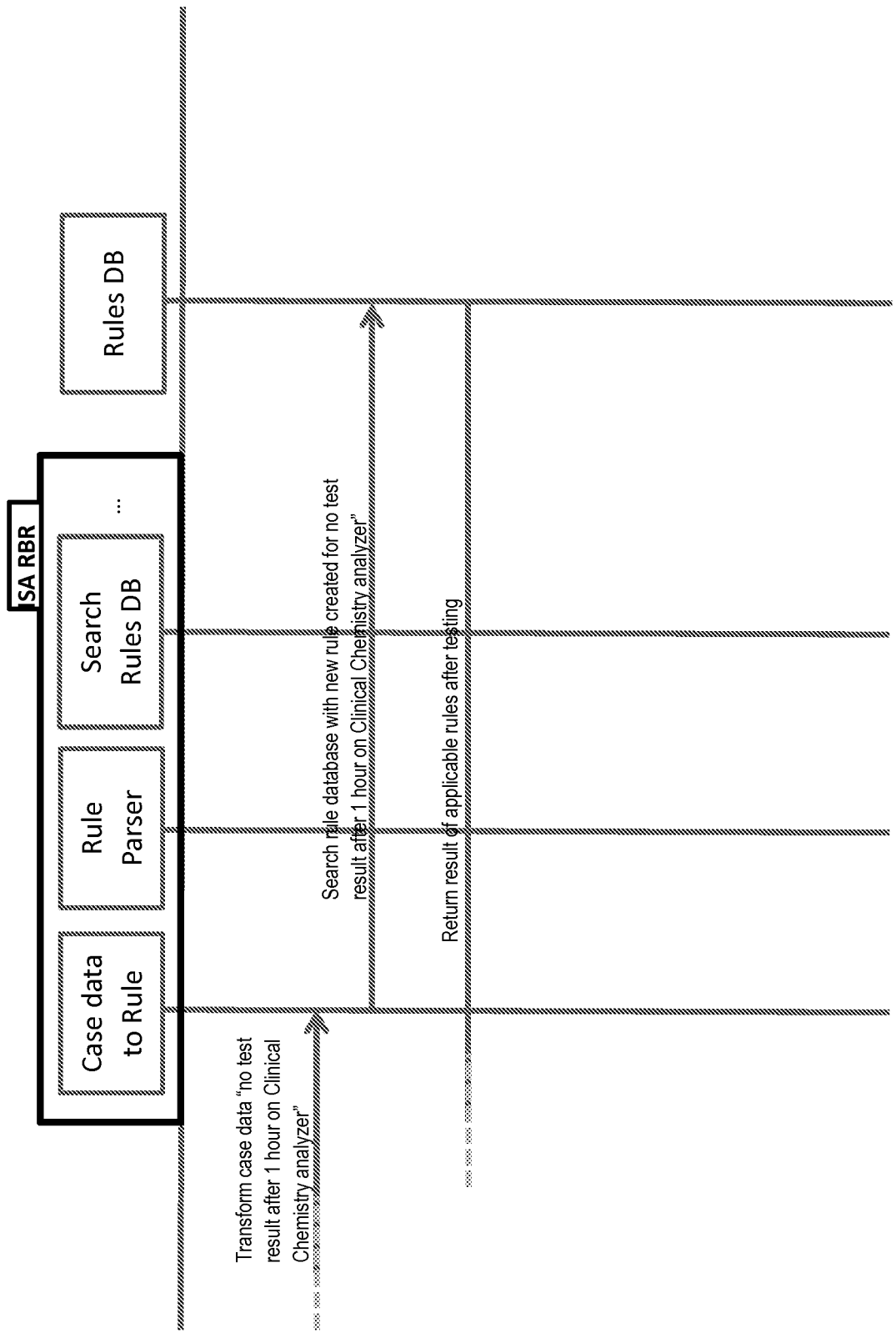
FIG. 24B shows a second portion message sequence diagrams for the RBR example, discussed with reference to FIGS. 19-22.

FIGS. 24A and 24B show message sequence diagrams for the RBR sample workflow discussed above, as it may be implemented in some embodiments.

The ISA Inference Engine improves service efficiency by reducing the number of unscheduled service visits by providing effective solution strategies. Solution strategies can be efficiently generated, tested, and updated, as well as distributed to operators, increasing the likelihood that an operator is able to obtain a correct solution strategy. The ISA Inference Engine also has a positive impact on product development through identification of product health issues early in product development and throughout the product life-cycle. Moreover, the ISA Inference Engine impacts customer service training through codification of customer service knowledge over time and across a fleet of instruments, allowing for the most effective solution strategies to be made available.

The ISA Inference Engine may be a processing device, computing device, processor, or the like for performing calculations and operations described herein. The ISA Inference Engine interfaces with various databases as described and may also interface with one or more other memory devices (not shown) such as read only memory (ROM), random access memory (RAM), and one or more optional non-transitory memory devices such as, for example, an external or internal DVD drive, a CD ROM drive, a hard drive, flash memory, a USB drive, or the like. The memory devices may be configured to include individual files and/or one or more databases for storing any software modules, instructions, or data.

Program instructions, software, or interactive modules for performing any of the functional steps associated with the processes as described above may be stored in the ROM and/or the RAM. Optionally, the program instructions may be stored on a tangible computer readable medium such as a compact disk, a digital disk, flash memory, a memory card, a USB drive, an optical disc storage medium, such as a Blu-Ray™ disc, and/or other recording medium.

A display interface may permit information from the ISA Inference Engine to be displayed on a display in audio, visual, graphic, and/or alphanumeric format. Communication with external devices may occur using various communication ports that may be attached to one or more communications networks, such as the Internet or a local area network, or directly to a portable computing device such as a notebook computer. An interface may allow for receipt of data from input devices such as a keyboard, a mouse, a joystick, a touch screen, a remote control, a pointing device, a video input device, an audio input device, and the like.

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

Figure 25:
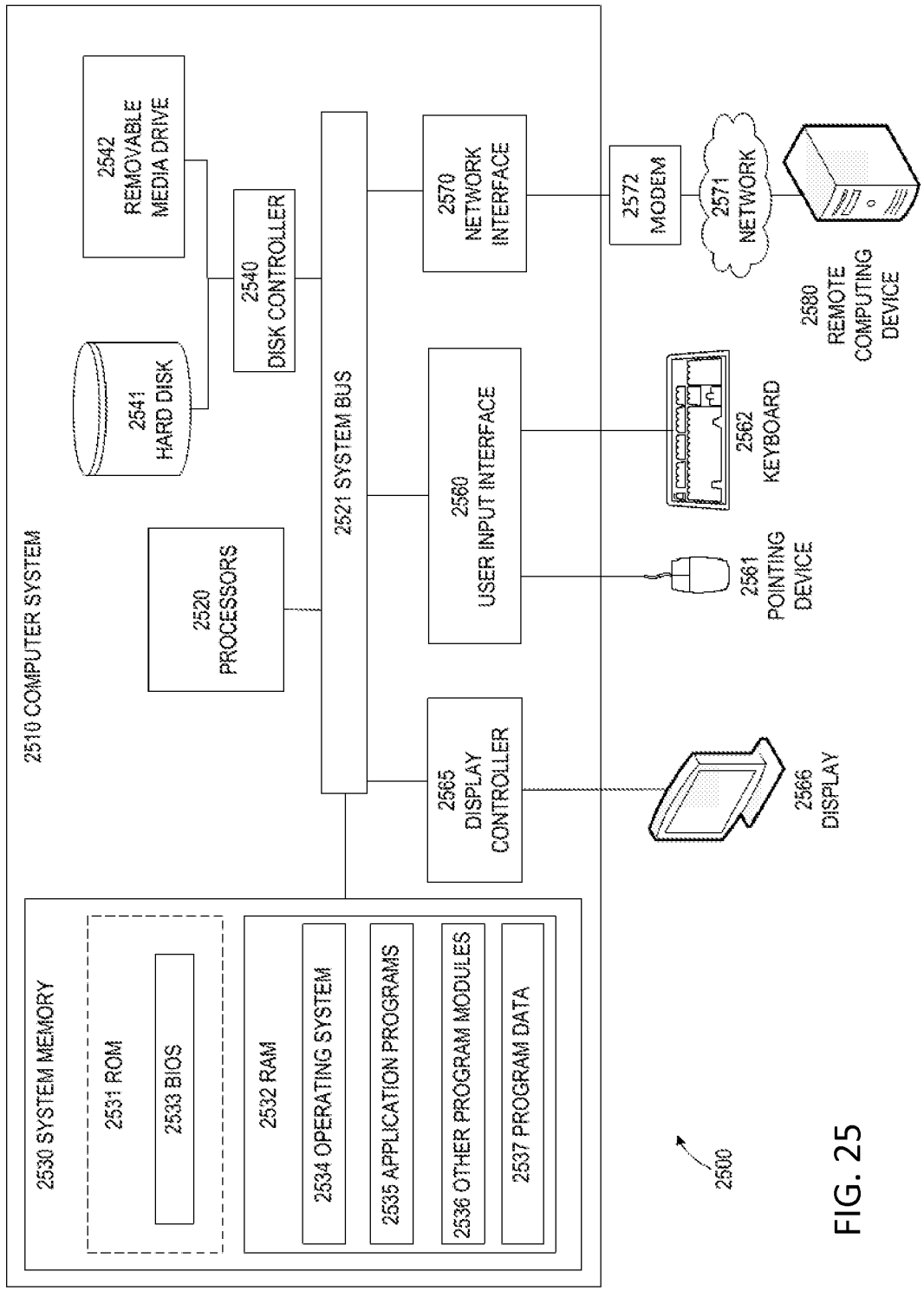
FIG. 25 illustrates an exemplary computing environment which may be utilized in some embodiments.

FIG. 25 illustrates an exemplary computing environment 2500 which may be utilized in some embodiments. The computing environment 2500 may include computer system 2510, which is one example of a computing system upon which embodiments of the invention may be implemented. Computers and computing environments, such as computer system 2510 and computing environment 2500, are known to those of skill in the art and thus are described briefly here.

As shown in FIG. 25, the computer system 2510 may include a communication mechanism such as a bus 2521 or other communication mechanism for communicating information within the computer system 2510. The computer system 2510 further includes one or more processors 2520 coupled with the bus 2521 for processing the information. The processors 2520 may include one or more central processing units (CPUs), graphical processing units (GPUs), or any other processor known in the art.

The computer system 2510 also includes a system memory 2530 coupled to the bus 2521 for storing information and instructions to be executed by processors 2520. The system memory 2530 may include computer readable storage media in the form of volatile and/or nonvolatile memory, such as read only memory (ROM) 2531 and/or random access memory (RAM) 2532. The system memory RAM 2532 may include other dynamic storage device(s) (e.g., dynamic RAM, static RAM, and synchronous DRAM). The system memory ROM 2531 may include other static storage device(s) (e.g., programmable ROM, erasable PROM, and electrically erasable PROM). In addition, the system memory 2530 may be used for storing temporary variables or other intermediate information during the execution of instructions by the processors 2520. A basic input/output system (BIOS) 2533 containing the basic routines that help to transfer information between elements within computer system 2510, such as during start-up, may be stored in ROM 2531. RAM 2532 may contain data and/or program modules that are immediately accessible to and/or presently being operated on by the processors 2520. System memory 2530 may additionally include, for example, operating system 2534, application programs 2535, other program modules 2536 and program data 2537.

The computer system 2510 also includes a disk controller 2540 coupled to the bus 2521 to control one or more storage devices for storing information and instructions, such as a hard disk 2541 and a removable media drive 2542 (e.g., floppy disk drive, compact disc drive, tape drive, and/or solid state drive). The storage devices may be added to the computer system 2510 using an appropriate device interface (e.g., a small computer system interface (SCSI), integrated device electronics (IDE), Universal Serial Bus (USB), or FireWire).

The computer system 2510 may also include a display controller 2565 coupled to the bus 2521 to control a display 2566, such as a cathode ray tube (CRT) or liquid crystal display (LCD), for displaying information to a computer user. The computer system includes an input interface 2560 and one or more input devices, such as a keyboard 2562 and a pointing device 2561, for interacting with a computer user and providing information to the processor 2520. The pointing device 2561, for example, may be a mouse, a trackball, or a pointing stick for communicating direction information and command selections to the processor 2520 and for controlling cursor movement on the display 2566. The display 2566 may provide a touch screen interface which allows input to supplement or replace the communication of direction information and command selections by the pointing device 2561.

The computer system 2510 may perform a portion or all of the processing steps of embodiments of the invention in response to the processors 2520 executing one or more sequences of one or more instructions contained in a memory, such as the system memory 2530. Such instructions may be read into the system memory 2530 from another computer readable medium, such as a hard disk 2541 or a removable media drive 2542. The hard disk 2541 may contain one or more datastores and data files used by embodiments of the present invention. Datastore contents and data files may be encrypted to improve security. The processors 2520 may also be employed in a multi-processing arrangement to execute the one or more sequences of instructions contained in system memory 2530. In alternative embodiments, hard-wired circuitry may be used in place of or in combination with software instructions. Thus, embodiments are not limited to any specific combination of hardware circuitry and software.

As stated above, the computer system 2510 may include at least one computer readable medium or memory for holding instructions programmed according to embodiments of the invention and for containing data structures, tables, records, or other data described herein. The term "computer readable medium" as used herein refers to any medium that participates in providing instructions to the processor 2520 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 2541 or removable media drive 2542. Non-limiting examples of volatile media include dynamic memory, such as system memory 2530. Non-limiting examples of transmission media include coaxial cables, copper wire, and fiber optics, including the wires that make up the bus 2521. Transmission media may also take the form of acoustic or light waves, such as those generated during radio wave and infrared data communications.

The computing environment 2500 may further include the computer system 2510 operating in a networked environment using logical connections to one or more remote computers, such as remote computer 2580. Remote computer 2580 may be a personal computer (laptop or desktop), a mobile device, a server, a router, a network PC, a peer device or other common network node, and typically includes many or all of the elements described above relative to computer system 2510. When used in a networking environment, computer system 2510 may include modem 2572 for establishing communications over a network 2571, such as the Internet. Modem 2572 may be connected to bus 2521 via user network interface 2570, or via another appropriate mechanism.

Network 2571 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 2510 and other computers (e.g., remote computer 2580). The network 2571 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 2571.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity. Also, while some method steps are described as separate steps for ease of understanding, any such steps should not be construed as necessarily distinct nor order dependent in their performance.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A method of providing dynamic analysis for troubleshooting in vitro diagnostics instrument issues, the method comprising:

receiving, at a first computing device in communication with a plurality of instruments, identification of an issue associated with a portion of an instrument of the plurality of instruments, the identification received from a second computing device in communication with the instrument;

accessing, by a central computing device, data from one or more databases, wherein the data comprises information previously received from the instruments specifying (i) one or more corrective actions previously executed by the instruments related to the issue and (ii) an indication of whether each of the one or more corrective actions was successful or unsuccessful in resolving the issue;

determining, by the central computing device, an ordering of the one or more corrective actions for resolving the issue, wherein the ordering of the one or more corrective actions is based on a probability that each of the one or more corrective actions will successfully solve the issue as indicated by the information previous received from the instruments; and providing, by the central computing device, the one or more corrective actions in the determined order to the second computing device to be displayed via a user interface at the instrument;

automatically determining, using one or more sensors on the instruments, that at least one of the one or more corrective actions successfully resolved the issue; and updating the data based on the issue and the at least one corrective action that successfully resolved the issue.

2. The method of claim 1, wherein the information previously received from the instruments further specifies operator input comprising at least one of: (i) feedback relating to the instrument; (ii) identification of the issue; and (iii) data indicating to a navigation path indicating steps taken to attempt to resolve the issue.

3. The method of claim 1, wherein the data further comprises at least one of calibration data, call center data, data logs from related instruments, vendor data, expert-built rule data, expert-built strategy data, and static troubleshooting data.

4. The method of claim 1, wherein the one or more databases are continuously updated to reflect issues and solutions.

5. The method of claim 1, further comprising incorporating the ordering of the one or more corrective actions for resolving the issue into a report.

6. The method of claim 1, further comprising:
receiving by the central computing device, identification of a successful corrective action from the one or more corrective actions from the associated computing device;
updating data in one or more of the one or more databases to indicate the successful corrective action; and
updating data in one or more local databases, each local database associated with a respective computing device on an instrument.

7. The method of claim 6, wherein each updating data step is performed in real-time or at regular intervals.

8. The method of claim 1, wherein the issue is one of software-related, hardware-related, or assay-related.

9. A system for providing dynamic analysis for troubleshooting in vitro diagnostics instrument issues, the system comprising:
a plurality of in vitro diagnostics instruments having sensors for monitoring corrective actions performed on the instruments;
one or more computing devices, each computing device in communication with an instrument of the plurality of in vitro diagnostics instruments and each computing device comprising a user interface having a display;
a central computing device in communication with the one or more computing devices;
one or more databases in communication with the central computing device;
wherein the central computing device is configured to:
receive identification of an issue associated with a portion of the instrument from the corresponding computing device in communication with the instrument;
access data from the one or more databases, wherein the data comprises information previously received from the instruments specifying (i) one or more corrective actions previously executed by the instruments related to the issue and (ii) an indication of whether each of the one or more corrective actions was successful or unsuccessful in resolving the issue;
determining an ordering of the one or more corrective actions for resolving the issue, wherein the ordering of the one or more corrective actions is based on a probability that each of the one or more corrective actions will successfully solve the issue as indicated by the information previously received from the instruments
provide the one or more corrective actions in the determined order to the computing device to be displayed via the user interface at the instrument;
determining that, according to sensor measurements at the instrument, at least one of the one or more corrective actions successfully resolved the issue; and
updating the data based on the issue and the at least one corrective action that successfully resolved the issue.

10. The system of claim 9, wherein the information previously received from the instruments further specifies operator input comprising one or more of (i) feedback relating to the instrument, (ii) identification of the issue, and (iii) data related to a navigation path indicating steps taken to attempt to resolve the issue.

11. The system of claim 9, wherein the data further comprises one or more of calibration data, call center data, data logs from related instruments, vendor data, expert-built rule data, expert-built strategy data, and static troubleshooting data.

12. The system of claim 9, wherein the one or more databases are continuously updated to reflect issues and solutions.

13. The system of claim 9, wherein the central computing device is further configured to incorporate the ordering of the one or more corrective actions for resolving the issue into a report.

14. The system of claim 9, wherein the central computing device is further configured to:
receive, from the corresponding computing device in communication with the instrument, identification of a successful corrective action from the one or more corrective actions;
update data in one or more of the one or more databases to indicate the successful corrective action; and
update data in one or more local databases, each local database associated with a respective computing device on a respective instrument.

15. The system of claim 14, wherein each updating data step is performed in real-time or at regular intervals.

16. The system of claim 9, wherein the issue is one of software-related, hardware-related, or assay-related.

* * * * *